(12) United States Patent
Osorio

(10) Patent No.: US 12,144,640 B2
(45) Date of Patent: *Nov. 19, 2024

(54) EPILEPTIC EVENT DETECTION BASED ON CORRELATION OF BODY SIGNALS

(71) Applicant: Flint Hills Scientific, L.L.C., Lawrence, KS (US)

(72) Inventor: Ivan Osorio, Leawood, KS (US)

(73) Assignee: Flint Hills Scientivic, L.L.C., Lawrence, KS (US)

( * ) Notice: Subject to any disclaimer, the term of this patent is extended or adjusted under 35 U.S.C. 154(b) by 686 days.

This patent is subject to a terminal disclaimer.

(21) Appl. No.: 17/241,279

(22) Filed: Apr. 27, 2021

(65) Prior Publication Data

US 2021/0244343 A1    Aug. 12, 2021

Related U.S. Application Data

(63) Continuation of application No. 14/208,466, filed on Mar. 13, 2014, now Pat. No. 10,993,652, which is a continuation-in-part of application No. 14/084,513, filed on Nov. 19, 2013, now Pat. No. 11,083,407.

(60) Provisional application No. 61/801,950, filed on Mar. 15, 2013, provisional application No. 61/793,292, filed on Mar. 15, 2013, provisional application No.
(Continued)

(51) Int. Cl.
*A61B 5/00* (2006.01)
*A61B 5/0205* (2006.01)
*A61B 5/11* (2006.01)

(52) U.S. Cl.
CPC .......... *A61B 5/4094* (2013.01); *A61B 5/0205* (2013.01); *A61B 5/1118* (2013.01); *A61B 5/4866* (2013.01); *A61B 5/7246* (2013.01); *A61B 5/7282* (2013.01)

(58) Field of Classification Search
CPC ... A61B 5/4094; A61B 5/0205; A61B 5/1118; A61B 5/4866; A61B 5/7246; A61B 5/7282
See application file for complete search history.

(56) References Cited

U.S. PATENT DOCUMENTS

2010/0121215 A1* 5/2010 Giftakis ............. A61N 1/36082
600/595
2011/0251468 A1* 10/2011 Osorio ................. A61B 5/7275
607/45
(Continued)

*Primary Examiner* — Tammie K Marlen
(74) *Attorney, Agent, or Firm* — CF3; Stephen Ci

(57) ABSTRACT

We report a method of a method for detecting an epileptic seizure, comprising providing a first body signal reference value; determining a current body signal value from a time series of body signals; comparing the current body signal value and the first reference value; determining a work level of the patient; determining whether the current body signal value comprises an ictal component, based on the work level and the comparing; issuing a detection of an epileptic seizure in response to the determination that the current body signal value comprises the ictal component; and taking at least one further action (e.g. warning, delivering a therapy, etc.), based on the detection. We also report a medical device system configured to implement the method. We also report a non-transitory computer readable program storage unit encoded with instructions that, when executed by a computer, perform the method.

13 Claims, 13 Drawing Sheets

Related U.S. Application Data

61/798,274, filed on Mar. 15, 2013, provisional application No. 61/785,429, filed on Mar. 14, 2013.

(56) References Cited

U.S. PATENT DOCUMENTS

| | | | | |
|---|---|---|---|---|
| 2011/0270095 | A1* | 11/2011 | Bukhman | A61B 5/349 |
| | | | | 607/45 |
| 2011/0295332 | A1* | 12/2011 | Osorio | A61B 5/4094 |
| | | | | 600/300 |
| 2012/0029390 | A1* | 2/2012 | Colborn | G16H 40/63 |
| | | | | 600/595 |

* cited by examiner

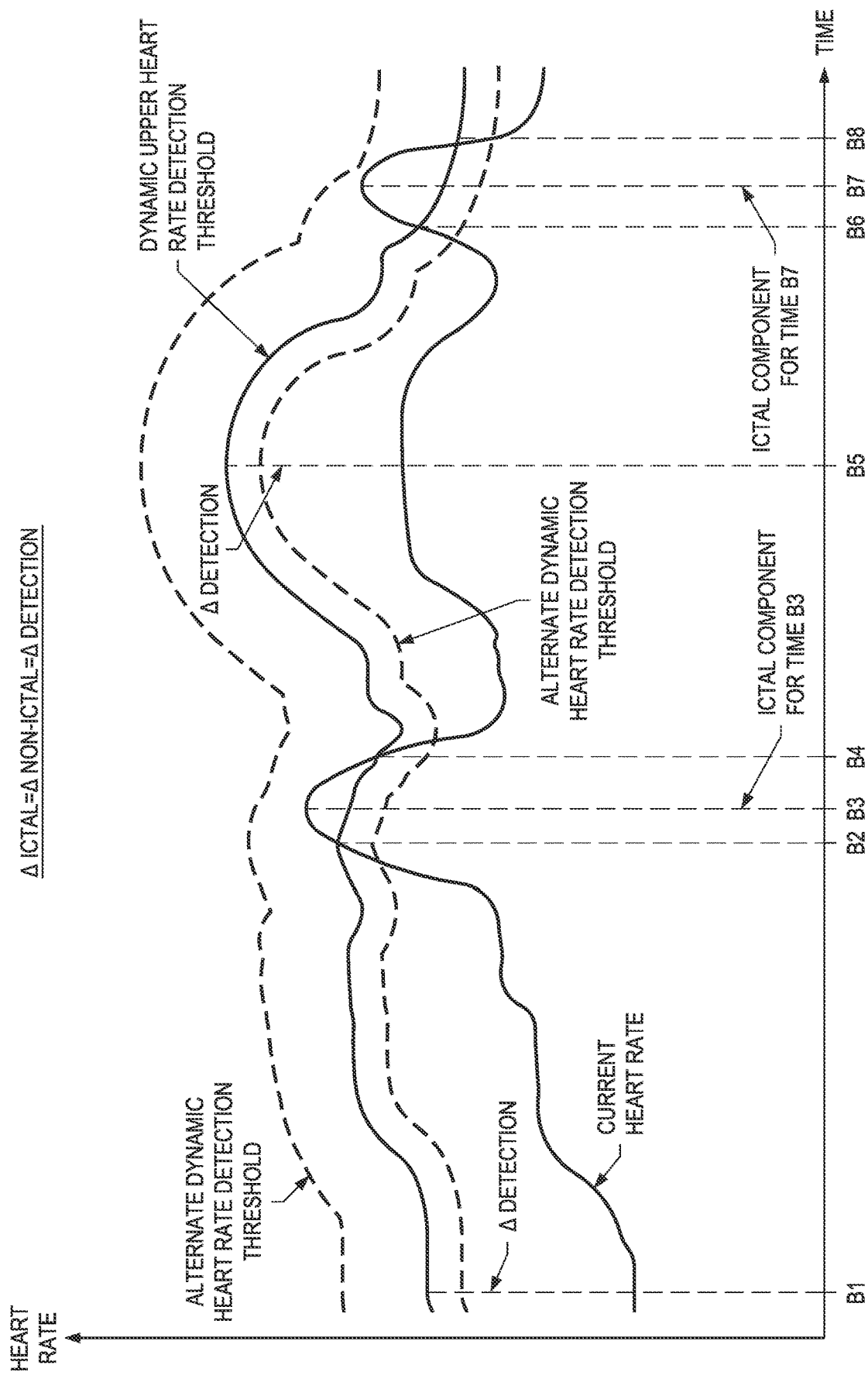

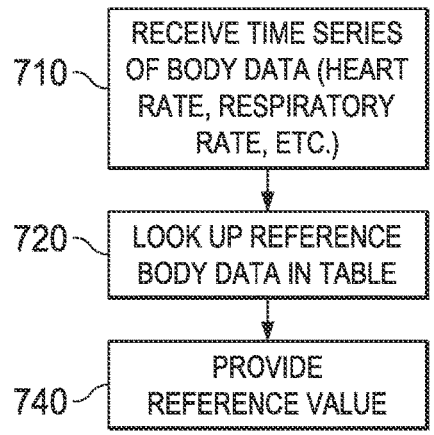

FIG. 7A

| WORK LEVELS | ACTIVITY LEVELS | FIRST BODY DATA VALUES | SECOND BODY DATA VALUES | THIRD BODY DATA VALUES | ∘∘∘ |
|---|---|---|---|---|---|
| WORK LEVEL - 1 | ACTIVITY TYPE - A REM SLEEP | FIRST BODY DATA VALUE - A | SECOND BODY DATA VALUE - A | THIRD BODY DATA VALUE - A | ∘∘∘ |
| WORK LEVEL - 2 | ACTIVITY TYPE - B NON-REM SLEEP | FIRST BODY DATA VALUE - B | SECOND BODY DATA VALUE - B | THIRD BODY DATA VALUE - B (e.g., RESPIRATION RATE = 11 BrPM) | ∘∘∘ |
| WORK LEVEL - 3 | ACTIVITY TYPE - C WALKING | FIRST BODY DATA VALUE - C (e.g., HEART RATE = 82 BPM) | SECOND BODY DATA VALUE - C | THIRD BODY DATA VALUE - C | ∘∘∘ |
| WORK LEVEL - 4 | ACTIVITY TYPE - D RUNNING | FIRST BODY DATA VALUE - D | SECOND BODY DATA VALUE - D | THIRD BODY DATA VALUE - D | ∘∘∘ |
| ∘∘∘ | ∘∘∘ | ∘∘∘ | ∘∘∘ | ∘∘∘ | |

FIG. 7B

EPILEPTIC EVENT DETECTION BASED ON CORRELATION OF BODY SIGNALS

CROSS-REFERENCE TO RELATED APPLICATIONS

This application claims priority to and is a Continuation of U.S. patent application Ser. No. 14/208,466, filed Mar. 13, 2014 (Now U.S. Pat. No. 10,993,652), entitled "Epileptic Event Detection Based on Correlation of Body Signals," which is a Continuation-In-Part of U.S. patent application Ser. No. 14/084,513, filed Nov. 19, 2013 (Now U.S. Pat. No. 11,083,407), entitled "Pathological State Detection Using Dynamically Determined Body Index Range Values," and claims priority to U.S. Provisional Patent Application Ser. No. 61/785,429, filed Mar. 14, 2013, U.S. Provisional Patent Application Ser. No. 61/793,292, filed Mar. 15, 2013, U.S. Provisional Patent Application Ser. No. 61/798,274, filed Mar. 15, 2013, and U.S. Provisional Patent Application Ser. No. 61/801,950, filed Mar. 15, 2013.

FIELD OF THE INVENTION

This disclosure relates to medical device systems and methods for detecting epileptic seizures in epilepsy patients based on patient work levels.

SUMMARY OF THE INVENTION

In some embodiments, the present disclosure relates to a method for detecting an epileptic seizure based upon a time series of body signals from a patient, comprising: obtaining said time series of body signals from said patient; determining a current body signal value from said time series; providing a body signal reference value; comparing said current body signal value and said body signal threshold; determining a work level of said patient using at least one of a kinetic signal, a metabolic signal, an endocrine signal, an autonomic signal, a blood pH signal, or a tissue stress signal; determining whether said current body signal value comprises an ictal component, based on said work level and said comparing; issuing a detection of an epileptic seizure in response to said determination that said current body signal value comprises an ictal component; and taking at least one responsive action to said issuing, wherein said responsive action is selected from issuing a warning of said detection, delivering a therapy, determining a severity of the detected epileptic seizure, and logging to memory one or more of the date and time of occurrence of the epileptic seizure, a severity of the epileptic seizure, a type of therapy delivered to treat the epileptic seizure, or at least one effect of a therapy delivered to treat the epileptic seizure.

In other embodiments, the present disclosure relates to a medical device system, comprising at least one first sensor configured to collect a time series of a body signal from a patient; at least one second sensor configured to sense a work level signal relating to said patient's work level; and a medical device, comprising: a body signal reference value module configured to provide at least a first body signal reference value; a current body signal module configured to determine a current body signal value from said time series; a comparison module configured to compare said current body signal value and said at least a first body signal reference value; a work level module configured to determine a work level of said patient, based at least in part on said work level signal; an ictal component module configured to determine whether said current body signal value comprises an ictal component, based on an output of said work level module and an output of said comparison module; an epileptic seizure detection module configured to issue a detection of an epileptic seizure, based on an output of said ictal component module indicative of said current body signal value comprising said ictal component; and at least one responsive unit for performing a responsive action based on the epileptic seizure detection module issuing a detection, wherein said responsive unit is selected from a warning unit configured to issue a warning signal of said epileptic seizure, a therapy unit configured to deliver a therapy for said epileptic seizure, a seizure severity unit configured to quantify a severity of said epileptic seizure, or a memory configured to log one or more of the date and time of occurrence of said epileptic seizure, a severity of the epileptic seizure, a type of therapy delivered, or at least one effect of a therapy delivered to treat the epileptic seizure.

In some embodiments, the present disclosure relates to a method for detecting an epileptic event in a patient's body, comprising receiving a first body signal during a first time period; receiving a second body signal during said first time period; determining whether there is a change in said first body signal during said first time period; determining whether there is a change in said second body signal during said first time period that correlates to said change in the first body signal, in response to determining that there is a change in said first body signal during said first time period; detecting an epileptic event in response to determining that there is not a change in said second body signal that correlates to said change in the first body signal; and performing a responsive action in response to detecting an epileptic event, said responsive action comprising at least one of delivering a therapy, providing a warning, or logging data relating to said epileptic event.

In some embodiments, the present disclosure relates to a non-transitory computer readable program storage unit encoded with instructions that, when executed by a computer, perform a method as described above.

BRIEF DESCRIPTION OF THE DRAWINGS

The disclosure may be understood by reference to the following description taken in conjunction with the accompanying drawings, in which like reference numerals identify like elements, and in which:

FIG. 3B shows an example of the ΔDetection, ΔNon-Ictal, and ΔIctal components of heart rates, according to some embodiments of the present disclosure;

FIG. 7A shows a flowchart depiction of a method, according to some embodiments of the present disclosure; and FIG. 7B depicts an exemplary work level, activity type, and body data value table usable in the method of FIG. 7A, according to some embodiments of the present disclosure.

Figure 1:
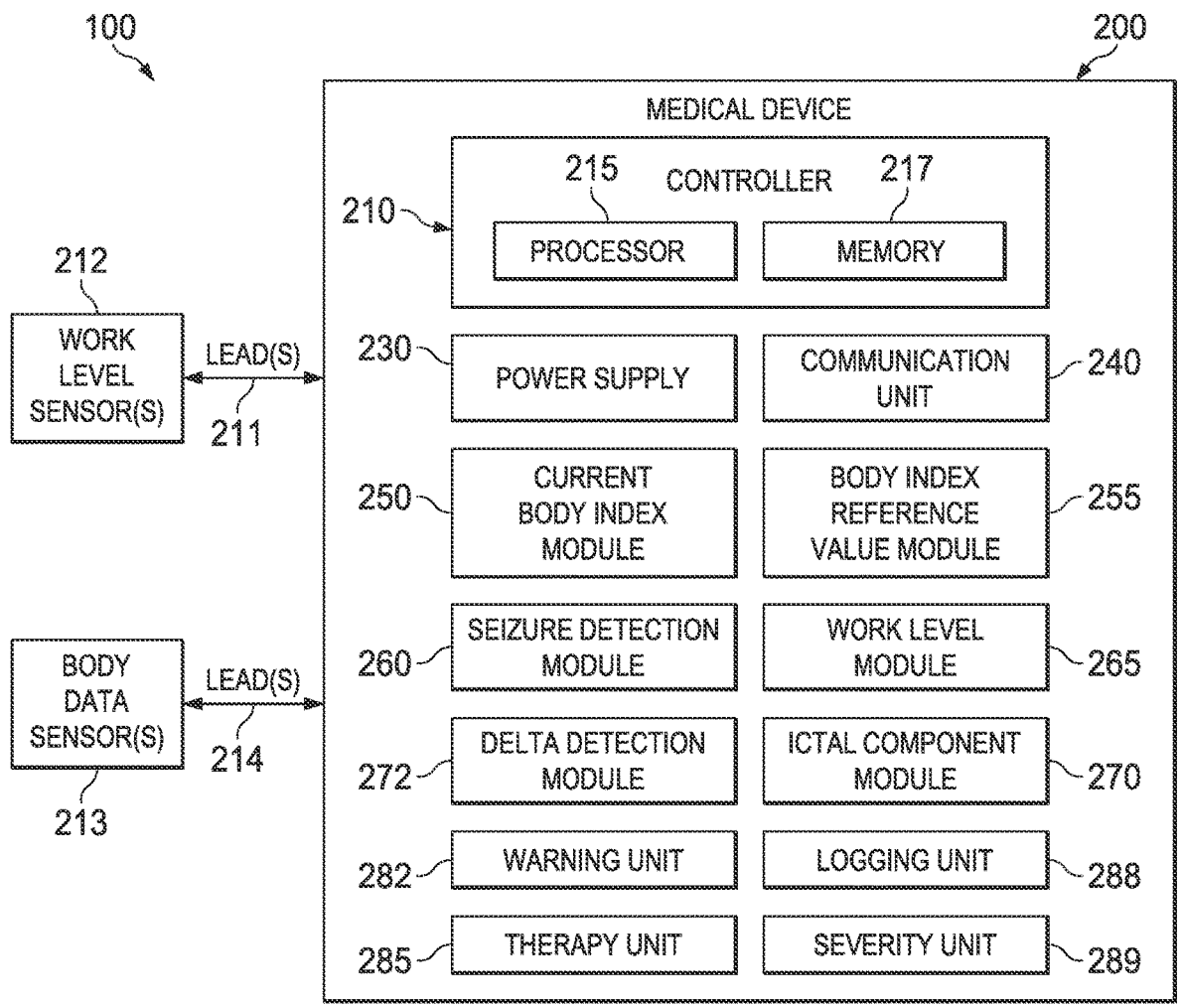
FIG. 1 shows a schematic diagram of a medical device system, in accordance with some embodiments of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

Embodiments disclosed herein provide for detecting an epileptic seizure based upon an ictal component or content of a body signal value of a patient. The ictal component may be determined based upon the body signal value, a reference value of the body signal, and a work level of the patient. One or more body signals of a patient may be acquired in a time series, from which a current body index value is determined and a work level of the patient may be determined based on the body index value relative to one of a body index reference value, a temporal fiducial or an activity level. The ictal component of the current body index value may be determined based upon the work level, as well as the current body signal value and the reference value. The magnitude of the ictal component may then be used to determine whether or not an epileptic seizure has occurred. If a seizure has occurred, a seizure detection may be issued. In response to issuing the seizure detection, a responsive action may be taken. The responsive action may include providing a warning, logging the epileptic event, providing a therapy, and/or providing a warning.

FIG. 1 shows a schematic representation of a medical device system, according to some embodiments of the present disclosure. The medical device system 100 may comprise a medical device 200, sensor(s) 212, and lead(s) 211 coupling the sensor(s) 212 to the medical device 200. In one embodiment, sensor(s) 212 may each be configured to collect at least one body signal (e.g., kinetic activity, differences in arterial and venous blood oxygen levels, etc.) from a patient relating to a work level of the patient. Generally, work level refers to a patient's energy consumption for any action/behavior performed by the patient, which may conveniently be measured, directly or indirectly, from body movement, oxygen consumption, brain activity, or the like. The classical definition of work (e.g., W=force×distance) is not excluded by this definition, but is only one (indirect) way of establishing the patient's energy consumption.

In one embodiment, the current body signal value (e.g., HR=82 bpm) may be considered a dependent variable and the work or activity level may be considered an independent variable. The value of the dependent variable (e.g., respiratory rate) may be plotted as function of the value of the independent variable (e.g., patient is jogging) and deviations from their physiological relationship (that are indicative of a pathological state) may be determined and used to take various responsive actions.

In another embodiment, the work or activity level may be the dependent variable and the body signal used as proxy (e.g. oxygen consumption; kinetic activity) to determine their values may be the independent variable. In some embodiments, each sensor(s) 212 may be selected from an accelerometer, an inclinometer, an electromyography (EMG) sensor, a muscle temperature sensor, an oxygen consumption sensor, a lactic acid accumulation sensor, a sweat sensor, a neurogram sensor, a force transducer, or an ergometer. In some embodiments, oxygen sensors, in/on the superior vena cava, in/on the jugular veins in/on the left ventricle, in/on the right ventricle, in/on the aorta or in/on one of its main branches, on the inferior vena cava or on the pulmonary arteries and veins may provide sufficient data to calculate total body (or brain) oxygen consumption, by measuring the difference in oxygen saturation or concentration between structures on the arterial compared to the venous side and based on said difference determine work level. Energy consumption by the patient may be derived from the oxygen consumption levels in some embodiments, while in other embodiments the oxygen consumption may be used as a measure of energy expenditure.

Various components of the medical device 200, such as controller 210, processor 215, memory 217, power supply 230, communication unit 240, warning unit 282, therapy unit 285, logging unit 288, and severity unit 289 have been described in other patent applications assigned to Flint Hills Scientific, LLC or Cyberonics, Inc., such as, U.S. Ser. No. 12/896,525, filed Oct. 1, 2010; U.S. Ser. No. 13/288,886, filed Nov. 3, 2011; U.S. Ser. No. 13/449,166, filed Apr. 17, 2012; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012; and U.S. Ser. No. 13/678,339, filed Nov. 15, 2012. Each of the patent applications identified in this paragraph is hereby incorporated herein by reference.

The medical device system 100 may further comprise at least one body data sensor 213, which may be coupled to medical device 200 by at least one lead 214, or wirelessly in some embodiments. The body data sensor(s) 213 may be configured to collect data from the patient relating to a time series of body signal values. The body signal may be selected from a cardiac signal (which may be used to determine one or more heart indices such as heart rate or heart rate variability), a blood pressure signal, a respiratory signal, a dermal signal, or a blood oxygen saturation signal, among others. The body signal may be processed to determine one or more body index values based upon the time series of body signal values.

In some embodiments, data relating to both a body signal (such as one of those listed above) and a work level may be collected by a single sensor or sensor type, i.e., in some embodiments, sensor(s) 212 and body data sensor(s) 213 may both refer to the same structure. In other embodiments, separate sensing elements may be used to sense patient work level and the patient body signal.

The medical device 200 may comprise a current body index module 250 configured to receive a time series of body data from the body data sensor(s) 213. The current body index module may process or use the time series of body data to determine (e.g., by calculation) one or more body indices from the time series of data. The current body index value may be based on a most recent time period of said time series comprising from about 1 sec (e.g., an instantaneous body signal value) to about 60 sec. In one example, a cardiac signal may be received from sensor(s) 213 and used to determine a short-term heart rate (e.g., a median heart rate in a time or number-of-beats window).

The medical device 200 may comprise a work level module 265 configured to determine a work level of the patient, based at least in part on a signal from work level sensor(s) 212. The work level signal may be at least one of a neurologic signal (e.g., a kinetic signal or a brain activity signal), a metabolic signal an endocrine signal, an autonomic signal, or a tissue stress signal. The work level determination may, in some embodiments, take into account one or more of a time of day, an indicator of the patient's overall health, an indicator of the patient's overall fitness, an indicator of the patient's level of consciousness (e.g., wakefulness v. sleep), an indicator of the patients activity level (e.g., walking at a certain pace on a level surface or on a 150 incline), the ambient temperature, the ambient humidity, altitude, or other patient or environmental conditions.

The medical device 200 may comprise a body index reference value module 255. The body signal reference value module 255 may be configured to determine at least a first body index reference value. The first body index reference value may correspond to a value of the first body index that would indicate a transition from a non-pathological state to a pathological state at a particular patient work level, as determined by the work level module 265. Where the reference value is specific to a particular work level, it may provide a pathological/non-pathological boundary for a particular patient state, e.g., resting while awake, asleep, exercising, etc., and may indicate an upper or lower current body index value boundary associated with a change from a non-pathological to a pathological state (e.g., an epileptic seizure). If the first body index reference value is a limit above which the patient would be expected to be in a pathological state (e.g., an upper epileptic seizure boundary), a current body index value exceeding the first body index reference value would be said to have an ictal component equal to the amount by which the current body index value exceeds the first body index reference value. A current body index value less than or equal to the first body index reference value would not have an ictal component. In some embodiments, the body signal reference value module 255 may be additionally configured to determine a second body index reference value, which may comprise, for example, a lower limit for a current body index, below which the patient would again be expected to be in a pathological state (e.g., a lower epileptic seizure boundary). In this case, a current body index value less than the second (lower) body index reference value would an ictal component equal to the amount by which the current body index value is less than the second body index reference value, arising from the current body index being pathologically low.

In addition to a patient work level, the first and/or second body index reference value(s) may further be based on one or more of a body signal, a time of day, the prevailing environmental conditions (e.g., temperature, humidity) an indicator of the patient's overall health, an indicator of the patient's overall fitness, or an indicator of the patient's wakefulness. The at least a first body index reference value may be determined for a first time period that is the same as, shorter than, or longer than a time period associated with the current body index value determined by the current body index module 250.

The medical device 200 may comprise an ictal component module 270 configured to determine whether the current body index value comprises an ictal component, based on a comparison of the current body index value and the body index reference value. The ictal component module 270 may be configured to determine whether the current body index value has an ictal component by determining whether a current body index value is above an upper non-pathological reference value or below a lower non-pathological reference value. The ictal component module 270 may further determine whether a current body index value comprises an ictal component based on one or more of a time of day, an indicator of the patient's overall health, an indicator of the patient's overall fitness, an indicator of the patient's wakefulness, a time since a most recent previous seizure, an average inter-seizure interval, a severity of a most recent previous seizure, or an average seizure severity.

The medical device 200 may comprise a seizure detection module 260 configured to detect a seizure, based on an output of the ictal component module 270 indicating that the current body index value comprises an ictal component.

Figure 2:
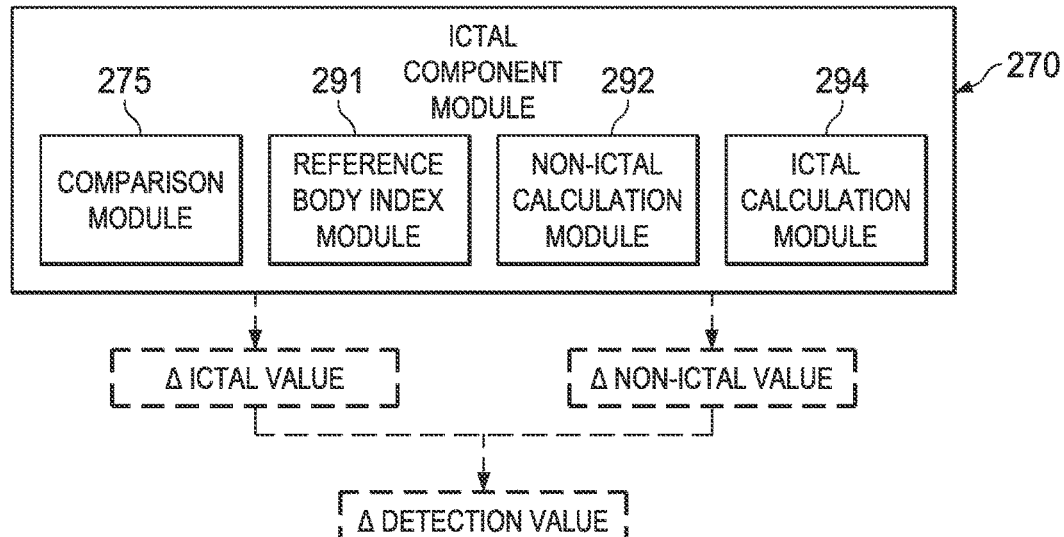
FIG. 2 shows a schematic diagram of a ictal component module of a medical device system, in accordance with some embodiments of the present disclosure.

FIG. 2 shows a schematic representation of the ictal component module 270 in greater detail, according to some embodiments of the present disclosure. The ictal component module 270 may comprise a reference body index module 291 configured to receive body index reference values from body index reference value module 255 and provide the reference values to other components of the ictal component module 270. The reference body index values may be specific for a particular non-pathological work level or state of the patient (e.g., sleeping, waking & ambulatory, vigorous exercise). The reference body index values may comprise, e.g., a measure of central tendency (e.g., median, quartile or some other statistical measure) for a microscopic (e.g., 1-10 sec.), mesoscopic (e.g., 11 sec.-24 hr) or macroscopic (e.g., >24 hr) time scale, and may optionally take into account patient or environmental conditions.

The ictal component module 270 may comprise a comparison module 275 configured to compare the current body signal value and the at least a first body signal reference value.

The ictal component module 270 may comprise a non-ictal calculation module 292 and an ictal calculation module 294. The non-ictal calculation module 292 may be configured to determine a non-ictal component of the patient's current body index value from information provided by the current body index module 250 and/or the reference body data table 291. The ictal calculation module 294 may be configured to determine an ictal component of the patient's body data from other information provided by the current body index module 250 and/or the reference body data table 291.

The ictal component module 270, as a result of operations of the non-ictal calculation module 292 and the ictal calculation module 294, may provide outputs comprising a ΔIctal (e.g., seizure) value and a ΔNon-Ictal (e.g., physical, cognitive or emotional activity) value, for use by the seizure detection module 260. Also, from the ΔIctal value and the ΔNon-Ictal value, a ΔDetection value may be determined.

Figure 3A:
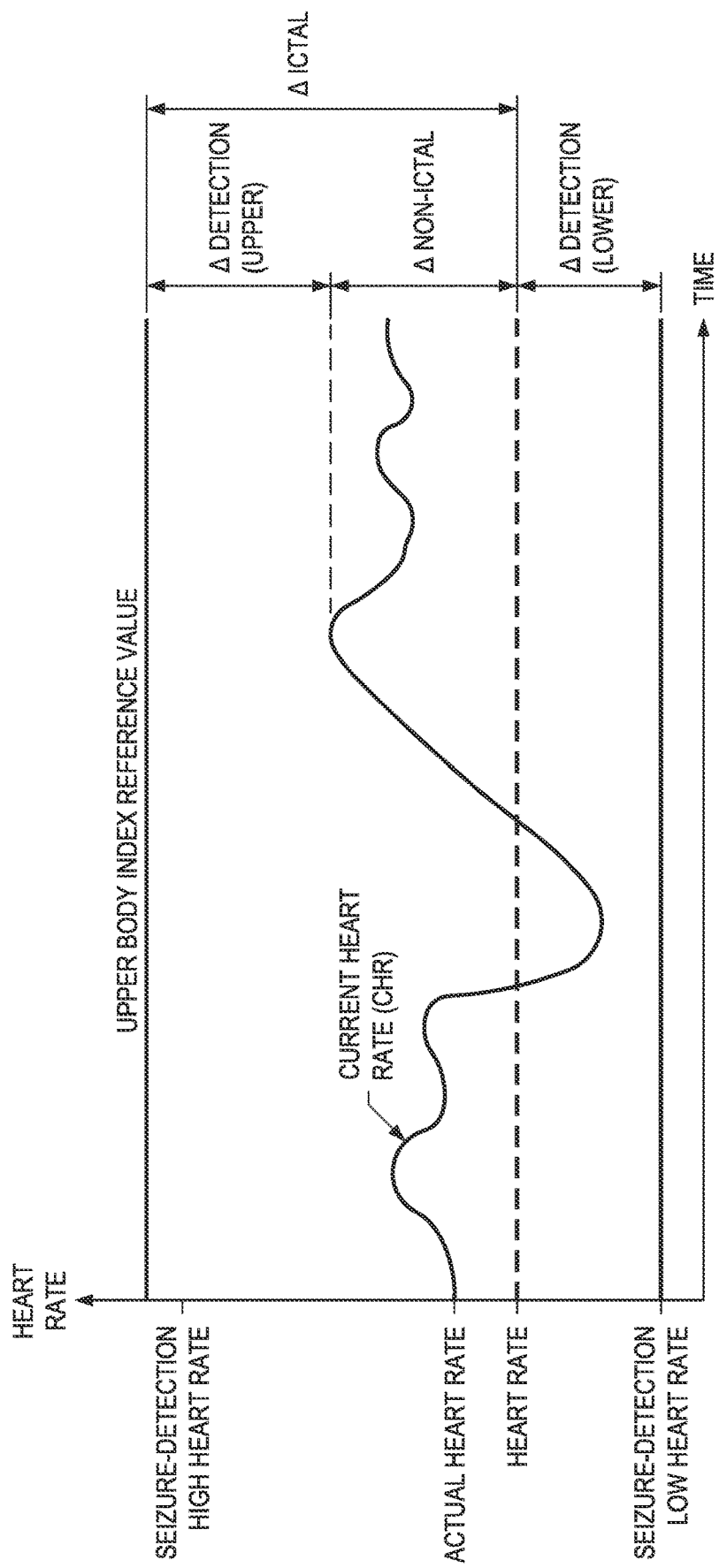
FIG. 3A shows an example of the ΔDetection, ΔNon-Ictal, and ΔIctal components of heart rates, according to some embodiments of the present disclosure.

FIG. 3A provides a simplified diagram of heart rate and seizure detection thresholds to illustrate certain concepts in connection with some embodiments of the present disclosure. FIG. 3A shows an exemplary reference heart rate (the patient's resting heart rate), a current ("actual") heart rate, a high (upper) seizure detection threshold (for seizures that increase the heart rate), a low (lower) seizure detection threshold (for seizures that decrease the heart rate), along with differences between the various heart rate and threshold values known as ΔDetection, ΔNon-Ictal, and ΔIctal, according to some embodiments of the present disclosure. The x-axis shows time, and the y-axis shows heart rate. The dashed line shows a resting heart rate (RHR) as an exemplary reference heart rate. Different or additional reference heart rates may also be used in certain embodiments. The resting heart rate (or other reference heart rate) is used as a fixed parameter for purposes of determining ΔNon-Ictal, and ΔIctal values. In some embodiments, RHR may be periodically updated to reflect longer-term changes in the patient's condition.

More information on measures of central tendency and time windows for determining body data values from a time series of body data can be found in U.S. Ser. No. 12/770,562, filed Apr. 29, 2010; U.S. Ser. No. 12/771,727; and U.S. Ser. No. 12/771,783, both filed Apr. 30, 2010, all three of which are hereby incorporated herein by reference.

In one embodiment, a patient's current heart rate (CHR) while at rest or physically active, and an upper seizure detection threshold heart rate (USDTHR) may be used to determine a value, ΔIctalU, that indicates an increase in heart rate associated with the onset of a seizure characterized by elevated heart rate according to the formula:

$$\Delta IctalU = USDTHR - CHR,$$

where the ictal component in CHR is either absent or the non-ictal component has been determined.

Depending on various factors, such as the level of motor activity (e.g., motionless, tonic or clonic activity or other movements) during a seizure, the increase in heart rate may be solely or primarily (e.g., in the case of seizures causing motionless tachycardia) attributable to the brain's abnormal electrical activity (e.g., the neurogenic component). With tonic-clonic seizures, on the other hand (which are the other end of the movement/kinetic spectrum from motionless seizures), heart or respiratory rate changes have neurogenic, exertional and metabolic components. It should be noted that the seizure detection threshold may or not represent the maximal increase in heart or respiratory rate caused by a seizure, but is instead an exogenous value that is selected based on clinical or safety considerations. For example, if seizure warning and blockage must (for therapeutic efficacy and/or safety considerations) take precedence over accuracy of detection, the detection threshold may be set at a level in which the ictal component is still low. The seizure detection threshold is different from the endogenous separatrix or threshold between body functions or signals without and with an ictal/seizure component (e.g., a change in their value or function caused by or associated with a seizure).

FIG. 3A illustrates the upper seizure detection threshold (USDTHR) as a fixed heart rate value, although in other embodiments (such as that shown in FIG. 3B) the seizure detection threshold may be dynamically adjusted. The patient's resting heart rate (RHR) value may be an instantaneous (e.g., present beat) rate or an average or median heart rate for a time window or a number-of-beats window, determined from data while the patient is at rest. Percentiles or deciles of resting heart rate data may be also used as RHR values in some embodiments.

A similar value, ΔIctalL ("delta ictal lower",) may be calculated to indicate a decrease in heart rate associated with a seizure characterized by reduced heart rate, according to the formula:

$$\Delta IctalL = CHR - LSDTHR,$$

where the ictal component in CHR is either absent or the non-ictal component has been determined to indicate the value in the reduction in heart rate solely attributable to the onset (e.g., the neurogenic component) of a seizure characterized by reduced heart rate for a resting patient. LSDTHR is a lower seizure detection heart rate threshold.

From the patient's current heart rate (CHR), and the resting heart rate (RHR), a difference referred to as ΔNon-Ictal defined in one embodiment as any increase in the current heart rate not caused by a seizure. More generally, the ΔNon-Ictal is defined as any change (positive or negative and of any magnitude or rate) in the value of a signal, caused by physiological activity.

This value corresponds to the magnitude of the increase in the patient's current heart rate above the resting heart rate, and indicates how much of the patient's heart rate is attributable to non-pathological physical activity (e.g., standing up from a sitting position, walking up stairs, exercising), cognitive activity (e.g., mental effort such as problem solving), and/or emotional activity (e.g., exposure to a fearful situation), by subtracting out the contribution of the RHR.

In one embodiment, the ΔNon-Ictal and the ΔIctal may be computed in reference to the resting heart rate or to other reference value as taught in in co-pending application Ser. No. 14/170,389, filed Jan. 31, 2014 entitled "Parametric Seizure Detection," which is hereby incorporated by reference herein in its entirety.

From the current heart rate (CHR) and one of: a) an upper seizure detection threshold USDTHR and/or b) a maximal change in the value (positive or negative) of a body signal caused by or associated with a seizure (ΔIctalmax), differences referred to as an upper ΔDetection (ΔDetectionU) may be calculated as:

$$\Delta DetectionU = USDTHR - CHR;$$

$$\Delta DetectionUmax = \Delta Ictalmax - CHR$$

As seen from FIG. 3A, ΔDetectionU is a measure of how far the patient's current heart rate (CHR) is below a (fixed or dynamic/adaptable) upper seizure detection threshold, USDTHR or the ΔDetectionL=CHR−LSDTHR. The greater the distance, the lower the probability of false negative detections. and the greater the probability of false positive detections. The smaller the distance, the higher the probability of false negative detections and the lower the probability of false positive detections. Thus, the magnitude of ΔDetectionU is an approximate measure of the likelihood (e.g., low) or of the probability (e.g., 60%) that an event may be missed (e.g., false negative detection) or that CHR values caused solely by physical or mental activity (ΔNon-Ictal) may be detected as a seizure (false positive detection).

The minimal possible heart rate may or may not be the same as the resting heart rate and the maximal possible heart rate may or may not be the same as the maximal ictal heart rate. The resting, ictal and exertional heart rates may vary as a function of multiple factors, making the ΔDetection variable in magnitude. In general, the lower the non-ictal heart (non-ictal heart rate encompasses resting and exertional heart rates) and the higher the ictal component, the larger the ΔDetection. A probability index for ictal detections may be estimated based on the values of the non-ictal components of a body signal and a correction or normalization may be introduced to decrease the number of FN detection when the non-ictal component is high or the ΔIctal is low.

A lower "ΔDetection" value may be determined from the CHR and a lower seizure detection heart rate threshold (LSDTHR) for seizures characterized by a decrease in heart rate that are often below the lower range of normal heart rate (e.g., the seizure may cause the heart rate to be lower than the normal resting heart rate). This value may be referred to as a lower delta detection or ΔDetectionL, and may be calculated as:

ΔDetectionL=CHR−LSDTHR;

ΔDetectionLmax=CHR+(−ΔIctalmax)

The magnitude of ΔDetectionL indicates how far the CHR is above the lower seizure detection threshold LSDTHR or the (−ΔIctalmax). The greater the distance, the lower the probability of false negative detections and the greater the probability of false positive detections. The smaller the distance, the higher the probability of false negative detections and the lower the probability of false positive detections. Thus, like ΔDetectionU, the magnitude of ΔDetectionL may be used to assess the likelihood (e.g., high or low) or of the probability (e.g., 20%) that an event may be missed (e.g., false negative detection) or incorrectly detected (false positive detection). The rate of the change in the value (positive or negative) of a body signal caused by a seizure may also indicate the likelihood or probability of false positive or false negative detections and provide insight into the time available for a detection.

Figure 6A:
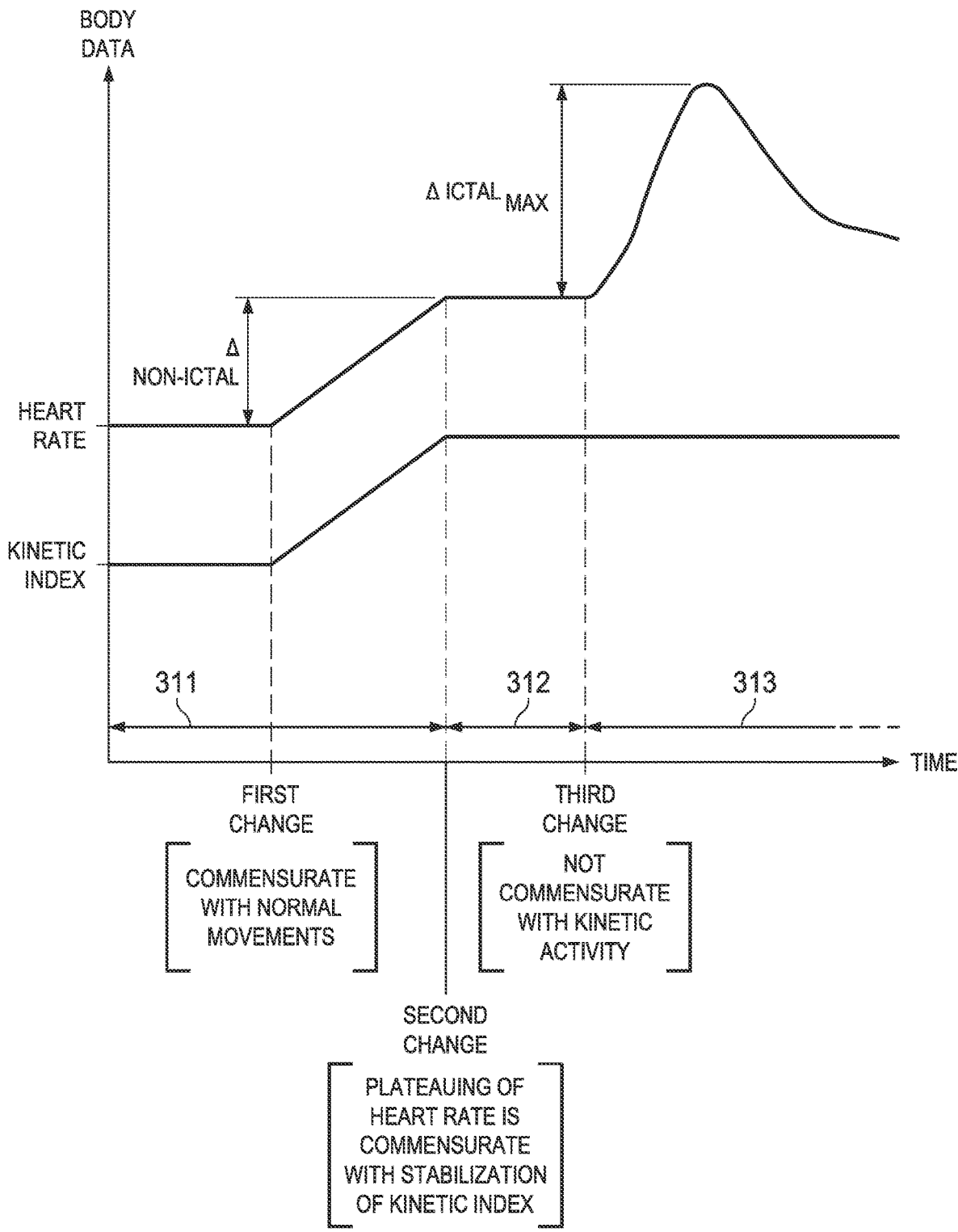
FIG. 6A shows a stylized depiction of a heart rate change in conjunction with a kinetic index, in accordance with a first embodiment.

As may be seen graphically in FIG. 6A, the value of upper or lower maximal change in signal value caused by or associated with a seizure (ΔIctalmax), may be determined by the equation:

ΔIctalmax=|Maximal signal value−ΔNon-Ictal|.

If ΔNon-Ictal=0, then ΔIctalmax=|Maximal signal value−CHR|, CHR as used in this embodiment indicates a value that remains stable and has not been subject to a physiological or pathological change immediately before or at onset of a seizure.

The magnitude of the difference in the value of a signal between its current value and the ΔIctalmax impacts the performance of any detection algorithm in terms of false positives, false negatives, and speed of detection. This difference, referred to herein as ΔDetectionmax, may be computed as ΔDetectionmax=|ΔIctalmax−CHR|.

ΔDetection may be a function of the value of the signal change at which detections are issued (based on a detection threshold value), and is referred to herein as ΔDetectionT, as shown by:

ΔDetectionT=|USDTHR−CHR|;

ΔDetectionT=|LSDTHR−CHR|.

Figure 6B:
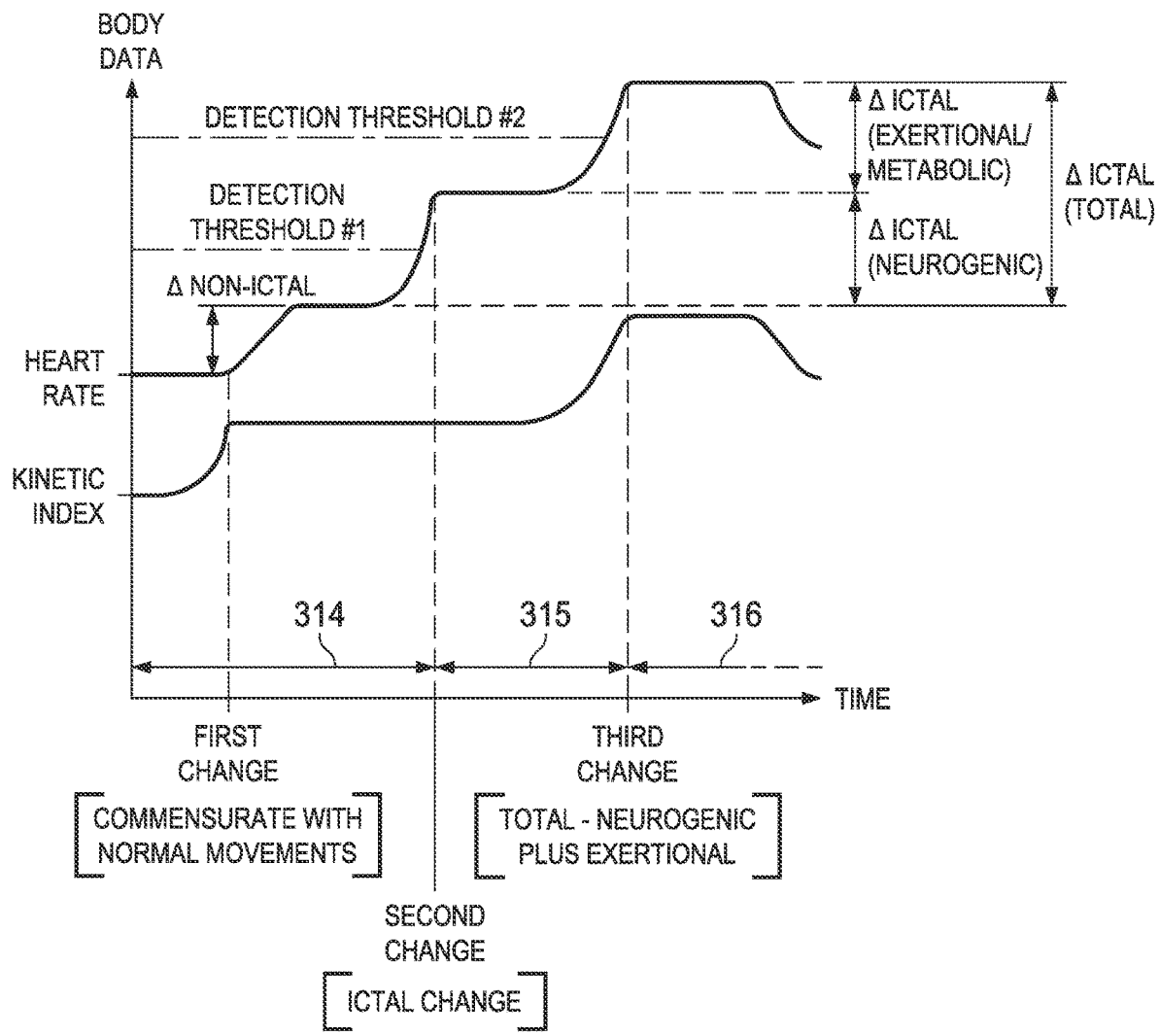
FIG. 6B shows a stylized depiction of a heart rate change in conjunction with a kinetic index, in accordance with a second embodiment.
Figure 6C:
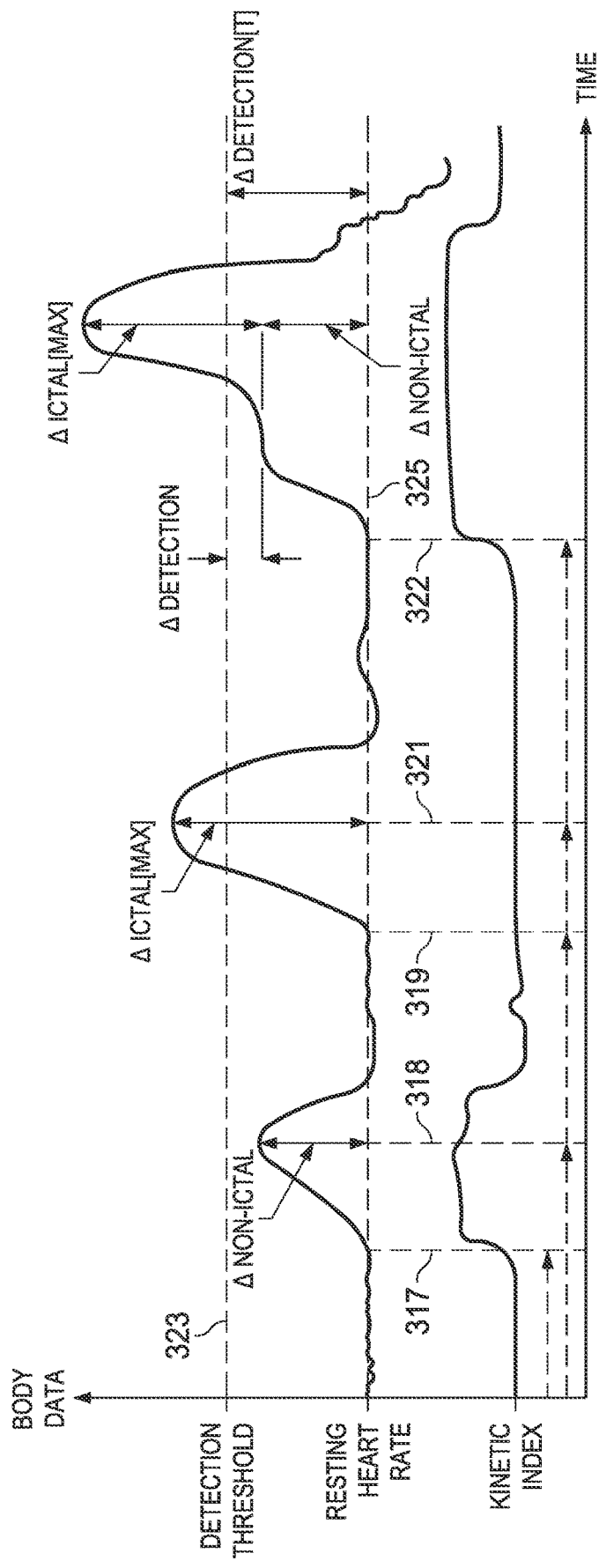
FIG. 6C shows a stylized depiction of a heart rate change in conjunction with a kinetic index, in accordance with a third embodiment.

Values of ΔDetectionU and ΔDetectionL may be computed as an arithmetical or algebraic, or absolute difference according to the foregoing formulae, and may be a valuable indicator or prognosticator of the performance (e.g., sensitivity, specificity, speed of detection) of seizure detection algorithms, and may be used to shape the performance of seizure detection methods. Moreover, knowledge of the changes or alterations in the magnitudes or patterns or rates of ΔDetectionmax or ΔDetectionT may be used to estimate in advance, the probability of correctness of event detections (for certain seizures using certain detection parameters) for optimization performance purposes. For the avoidance of confusion, ΔDetectionmax is the maximal increase in a body signal (e.g., from the pre-ictal body signal value) caused by a seizure and ΔDetectionT is the magnitude of the change between the pre-ictal body signal value and the detection threshold. For example, in the case of ΔDetectionmax=+35 bpm, the ΔDetectionT may be anywhere between +1 bpm and +35 bpm. Note that ΔDetectionmax is equal to ΔIctalmax. Changes in the value of a body signal may be classified as either physiological/non-ictal (ΔNon-Ictal) or pathological/ictal (ΔIctal) by cross-referencing the body signal value (e.g., heart rate) used for detection with at least one different feature (e.g., EKG morphology) of the same body signal (e.g., cardiac) or with at least one different signal (e.g., kinetic activity, respirations, EEG, etc.). For example, FIGS. 6A-C show that, in a patient with epilepsy, heart rate is the signal used for seizure detection, the classification of changes in its value as either or non-ictal may be accomplished by concurrently/simultaneously monitoring kinetic activity (body movements, posture, etc.) with a suitable device such as an accelerometer. FIGS. 6A-C illustrate how the dynamic interrelation between ΔNonictal, ΔIctal, ΔDetection, their magnitudes and rates of occurrence, and the value at which the detection threshold is set.

Although shown as a constant value in FIG. 3A, seizure detection thresholds need not be constant (e.g., the same value regardless of the patient's physical, cognitive or emotional activity levels, conditions, etc.), nor comprise a single value; multiple thresholds may be set, each corresponding to a certain probability of correctness of detection or positive predictive value or speed of detection. In some embodiments, a seizure detection threshold may vary on a preprogrammed basis according to a predetermined protocol. Alternatively, a seizure detection threshold may be dynamically adjusted based at least in part on one or more of patient work levels or activity levels, a time of day, an indicator of the patient's overall health, an indicator of the patient's overall fitness, level of consciousness, the magnitude of changes of ictal and non-ictal components (as explained hereinafter) of a body signal, a time since a most recent previous seizure, an average, variance or some other measure of inter-seizure interval, a severity of a most recent previous seizure, or an average or some other measure of seizure severity.

In alternative embodiments, a detection threshold (or declarations of a detected seizure) may be altered based at least in part on ΔDetection values. For example, if heart rate is the signal being used for seizure detection, the CHR immediately before seizure onset was 80 bpm, and the magnitude of a ΔDetectionmax is +35 bpm, a seizure would be declared only when the heart rate increased sufficiently to reduce the value of ΔDetectionmax to 0 (which occurs when the CHR reaches the maximum ictal value. However, in some embodiments, seizures may be declared well before (e.g., in this example when ΔDetectionT=+5 bpm) the heart rate reaches the ΔDetectionmax, for safety and/or therapeutic efficacy reasons. For example, if a patient who has seizures that render the patient unaware and/or unresponsive is operating a motor vehicle, early warning (before loss of cognitive and other brain functions results in unawareness or unresponsiveness) is desirable for safety reasons. Under this circumstance, a detection may be issued for ΔDetectionT=+5 bpm to provide a margin of safety to protect the patient and/or others. On the other hand, in other embodiments, e.g., if the same patient is lying down in bed so safety risks are minimal and automated therapy is associated with certain adverse effects, a seizure detection may be issued (or therapy or a warning provided) only when ΔDetectionT=+25 bpm to minimize the probability of false positive detections and the anxiety to the patient or caregivers associated with an erroneous detection.

Referring to FIG. 3B, in one embodiment, dynamic upper and lower seizure detection thresholds (e.g., USDTHR and LSDTHR, although for illustrative purposes only USDTHR curves are illustrated in FIG. 3B) may be established as the patient's non-pathological work level changes over time. For example, at point B1 in FIG. 3B, the ΔDetectionU is relatively large, as the ΔNon-ictal is small as it would correspond to a period of rest or reduced motor activity. Conversely, at point B5, the ΔDetectionU is smaller relative to point B1, which corresponds to a period of exercise.

In some embodiments, seizure detection thresholds may vary on a preprogrammed basis based at least in part on time of day, activity/work level and/or other considerations. In some embodiments, seizure detection thresholds may be dynamically adjusted based at least in part on one or more of an indicator of the patient's overall health, an indicator of the patient's overall fitness, an indicator of the patient's wakefulness, a time since a most recent previous seizure, an average inter-seizure interval, a severity of a most recent previous seizure, or an average seizure severity.

Various thresholds for issuing a seizure detection may be set according to the clinical application and the patient's characteristics. In general, the larger the ΔDetection (defined as the difference between the current body signal/index value and one of the maximal change in the signal/index caused by a seizure, or the maximal value (e.g., in the case of HR: 220 bpm-age) attainable by a seizure. More than one threshold may be set and each threshold may be associated with a qualitative statement of likelihood (e.g., low, high) or with a probability estimate (e.g., 60%) based on historical data about the performance (false positive, false negative, speed of detection) of a certain threshold. When HR is the signal/index used for seizure detection, the ictal threshold HRic may be set as low as ΔNon-ictal+1 or as ΔNonictal+ non-integer value. In addition, a seizure detection signal may be generated and a seizure event may be logged.

In FIG. 3B, the CHR has an ictal component 1) from point B2, at which the current heart rate first crosses the heart rate's non-ictal component, to point B4, at which the current heart rate falls back below the non-ictal component of the HR and 2) from point B6 to point B8. At a specific point B3 between points B2 and B4, or B7 between points B6 and B8, the magnitude of the ictal component may be determined by the formula ΔIctal=CHR−ΔNon-Ictal.

The ictal component of heart rate may provide an indication of the severity of a detected seizure. In some embodiments, epileptic seizures may be characterized by the magnitude and/or rate (e.g., slopes) of the ictal component changes from the onset of the seizure until the end of the seizure. In particular, one or more of the shape, duration, and magnitude of the ictal component may be used to characterize and/or classify the seizure event. For example, in FIG. 3B, the seizures associated with points B2-B4 and B6-B8 may be characterized by the shape (e.g., area under the curve or height×base) of the ictal component envelope.

In some embodiments, more than one threshold may be set. Each such threshold may be associated with a qualitative statement of likelihood (e.g., low, high), or with a probability or a percentile value (e.g., 80th) of the particular threshold among a plurality of threshold values associated with similar activity levels, times of day, or historical data about the performance (false positive, false negative, speed of detection) associated with each threshold value.

Figure 3C:
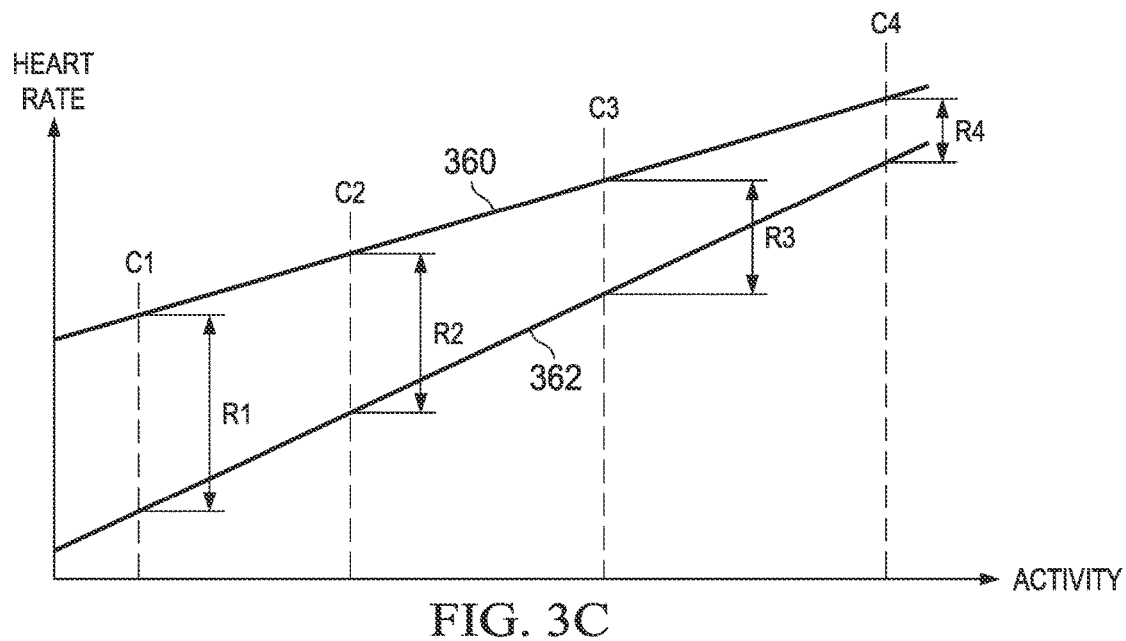
FIG. 3C shows an example of the ΔDetection, ΔNon-Ictal, and ΔIctal components of heart rates, according to some embodiments of the present disclosure.

FIG. 3C shows an idealized dynamic relationship between non-pathological/non-ictal patient activity levels (e.g., as determined from a tri-axial accelerometer) on the x-axis and an exemplary body index (heart rate) on the y-axis. It should be appreciated that in other embodiments, different body indices may be used instead of, or in addition to, heart rate to detect seizures, and dynamic relationships similar to that show in FIG. 3C may be provided. Although non-pathological activity level is shown in FIG. 3C as a single continuous parameter along the x-axis, a plurality of discrete activity levels or states (e.g., resting lying down, resting sitting, working sitting, walking slowly, walking briskly, running, etc.) may also be used to correlate heart rate (or another body index) to activity levels in some embodiments of the invention. Because current heart rate is a variable that may be influenced by many different factors besides activity levels (e.g., the patient's age, sex, body mass index, fitness level, hydration status, environmental conditions such as temperature, humidity, emotional activity, etc.) a particular activity level may correspond to a current heart rate anywhere within the associated non-pathological/non-ictal heart rate range.

As used interchangeably herein, two body signal values (the dependent and independent variables) may be deemed to be "correlated," "coupled," or "commensurate" with one another if under physiological conditions the direction (e.g., increase or decrease), latency, magnitude, rate, and/or duration of the dependent variable as a function of the independent variable are preserved or maintained. For example, if heart rate (HR) increases at a certain rate and by a certain magnitude each time a healthy subject performs the same physical activity (a positive correlation) under physiological conditions, the expected changes in certain body signals for a certain activity type and level are commensurate with those observed. In certain cases, the value of the dependent and independent variables may change in opposite direction (e.g., as one increases, the other decreases). For example, as luminance decreases, the size of the pupils increases.

FIG. 3C shows one embodiment of an activity-based, non-pathological heart rate range, (y-axis), corresponding to a certain activity level (x-axis) bounded by an upper HR boundary line 360 and a lower HR boundary line 362. Upper heart rate boundary line 360 may separate, with satisfactory specificity, certain seizure classes (e.g., convulsions) with signal values above line 360 at the highest levels (e.g., C3-4)

and partial seizures, also with satisfactory specificity, at low-to-mid activity levels (e.g., C1-2) from certain physiological states or activity levels (below the line). The lower heart rate boundary line 362 separates seizures associated with a certain degree of bradycardia (heart rates below line 362) from resting (non-pathological) states (above the line 362 and below line 360). Thus, in one embodiment, both upper and lower boundary lines 360, 362 may be considered as ictal threshold for a given activity level (i.e., a given point along the x-axis). In the case of epileptic seizures, upper HR boundary line 360 may be considered as an ictal heart rate threshold for seizures having a pathological increase in heart rate, and lower HR boundary line 362 may be considered as an ictal heart rate threshold for seizures characterized by an abnormal or pathological decrease in heart rate.

The region between the upper and lower boundary lines 360, 362 defines a region in which the patient's heart rate may be considered as non-pathological under normal/non-extreme patient and environmental conditions. Both the upper and lower ictal boundaries 360, 362 of the non-ictal heart rate region increase as activity level increases (e.g. from a sleep state to a resting, awake state, or from left to right on the x-axis) and reach their highest values for strenuous activity (e.g., strenuous exercise, point C4). In addition, the width of the non-pathological heart rate range (the area between the upper and lower ictal heart rate thresholds 360, 362 narrows as activity levels and heart rates increase, which is consistent with the known reduction in heart rate variability at high levels of exertion.

When the patient is in a non-pathological state (e.g., when an epileptic patient is not having a seizure), for a particular activity level the patient's short-term heart rate should fall within a non-pathological heart rate range associated with that activity level. Referring to FIG. 3C, at a particular activity level C1—corresponding, for example, to a sleeping activity level—a non-pathological HR range R1 may be determined between upper and lower ictal heart rate thresholds 360 and 362. Another non-pathological heart rate range R2 may be established by upper and lower boundaries 360 and 362 for, e.g., resting awake activity level C2. At activity levels C3 and C4, corresponding to moderate and strenuous exercise, respectively, corresponding non-pathological HR ranges R3 and R4 may be determined from upper boundary 360 and lower boundary 362. As noted, the width of the non-pathological heart rate ranges decrease as activity levels increase, and thus R1>R2>R3>R4.

Figure 3D:
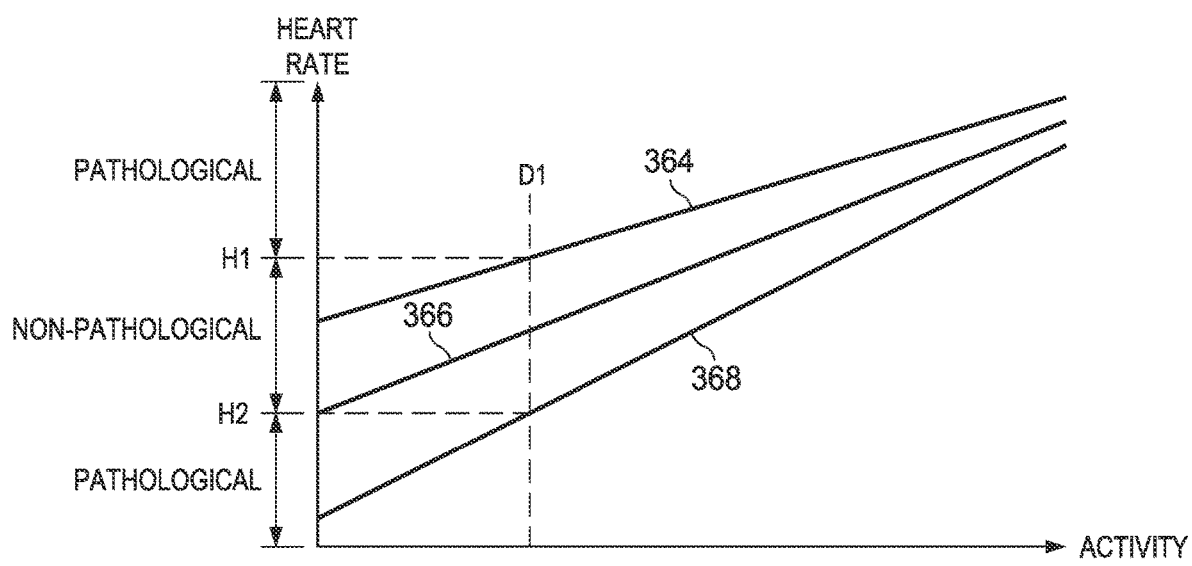
FIG. 3D shows an example of the ΔDetection, ΔNon-Ictal, and ΔIctal components of heart rates, according to some embodiments of the present disclosure.

Referring to FIG. 3D, in another embodiment, non-pathological heart rate ranges as a function of activity level are determined by upper and lower boundaries 364 and 368. For a particular activity level D1, the non-pathological range lies between heart rate H1 and H2. At heart rates above H1, the patient's heart rate may be pathologically high (e.g., when the patient is having a seizure characterized by elevated heart rate), while at heart rates below H2, the patient's heart rate may be pathologically low (e.g., when the patient is having a seizure characterized by reduced heart rate).

Upper and lower non-pathological heart rate boundaries 364, 368 may be determined from a given patient or from patient population data (taking into account, in some embodiments, age, gender, health status, fitness level, etc.) and stored in a memory of a remote, or implantable or body-worn medical device. For convenience, boundaries 364, 366, and 368 are shown as straight lines. The person of ordinary skill in the art would appreciate that in an actual embodiment these boundaries may be non-linear. When needed, the heart rate data may be retrieved from the memory for use by the medical device to determine whether the patient's heart rate is within a non-pathological range appropriate in view of the patient's activity level. Alternatively, heart rate ranges may be determined by calculation from a formula based on the patient's activity level (e.g., kinetic or based on oxygen consumption), which may optionally take into account one or more additional endogenous factors such as the patient's age, sex, fatigue level, hydration level, general health, and physical fitness, or exogenous factors such as the time of day, humidity, temperature, altitude, etc.

Upper and lower boundaries 364, 368 may in some embodiments be determined empirically from patient-specific data collected over time for a variety of activity levels. For example, the patient may be subjected to one or more tests such as a walking test on a treadmill, with heart rates determined at each of a variety of different activity levels (e.g., as determined from one or more of a three-dimensional accelerometer, an electromyogram, gyroscope, and/or imaging devices such as a camera). Other activity level tests may be performed to determine upper and lower boundaries 364, 368. In one embodiment, upper non-pathological boundary 364 may be determined as an upper percentile value (e.g., the 90th, 95th, or 99th percentile) of the non-pathological heart rates measured at a number of different times corresponding to the particular activity level. Thus, a linear or a polynomial may be fitted through the target upper percentile values over a range of activity levels to obtain the upper boundary 364. Similarly, another polynomial may be fitted through a target percentile value (e.g., 5th, 2nd, 1st) to obtain the lower boundary 368.

Additional curves may be determined by fitting polynomials to additional target percentile values of the activity level/HR data. Referring again to FIG. 3D, a median boundary line 366 may be determined by fitting a polynomial through, for example, the 50th percentile values of heart rate across a range of activity levels. Additional percentile values (e.g., an upper quartile or 75th percentile, a lower quartile or 25th percentile, etc.) may be determined similarly (not shown in FIG. 3D). In one hypothetical example, the region between median boundary line 366 and upper ictal threshold line 364 may be considered as a hypothetical ΔDetectionU region, since for each activity level it is defined by the difference between the upper ictal threshold and an expected (median) nonictal value of heart rate (although not an actual ΔDetectionU region because median boundary line 366 is not an actual (current) heart rate as required of true ΔDetectionU values). Similarly, the region between median boundary line 366 and lower ictal threshold line 368 may be considered as a hypothetical ΔDetectionL region, sine it is defined by the difference between the lower ictal threshold and an expected (but not an actual) nonictal value of heart rate.

In some embodiments of the present invention, upper and lower boundaries of physiological body signal values may be determined so that a value above or below said boundaries indicates the transition into one or more pathological states. For example, separate upper and lower heart rate boundaries of physiological body signal values as a function of activity level and/or other factors may be determined for simple partial seizures, complex partial seizures, or generalized tonic-clonic seizures, among others. Without being bound by theory, these upper and lower boundaries for each seizure type may be determined as specific percentile value curves for a specific body index used to detect seizures as a function of activity levels from a population of values at each activity level or state, as described above. For example, in one embodiment a pathological upper boundary for a simple partial seizure may be above the 90th percentile value for a particular activity level, while a pathological upper boundary for a complex partial seizure may be above the 95th percentile value for a particular activity level.

In some embodiments, upper and lower ictal threshold boundaries for simple partial and complex partial seizures may be determined based on activity levels, oxygen consumption or the results of a responsiveness or awareness test. For example, where the awareness test indicates that the patient has not lost awareness, the heart rates measured while the patient remains aware may be used (along with activity levels) as data to determine upper and lower heart rate boundaries for simple partial seizures. When and if the patient loses awareness, the data of heart rate and activity level may be used to determine upper and lower activity level heart rate boundaries for seizures associated with loss of awareness, such as complex partial, complex partial with secondary generalization, or generalized seizures.

Figure 3E:
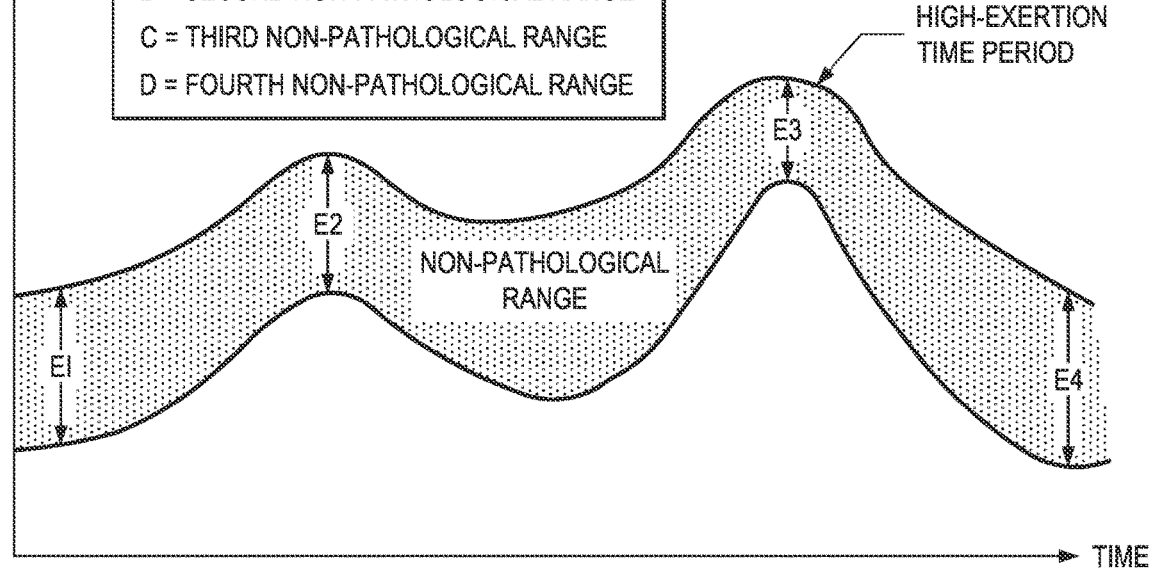
FIG. 3E shows an example of the ΔDetection, ΔNon-Ictal, and ΔIctal components of heart rates, according to some embodiments of the present disclosure.
Figure 3F:
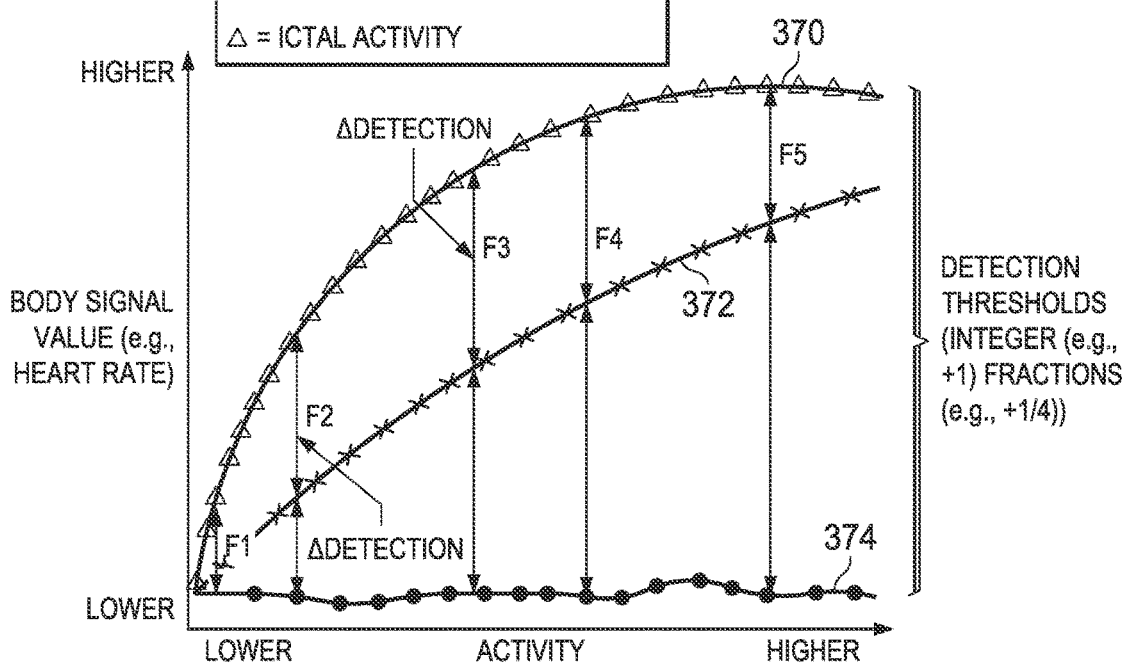
FIG. 3F shows an example of the ΔDetection, ΔNon-Ictal, and ΔIctal components of heart rates, according to some embodiments of the present disclosure.
Figure 3G:
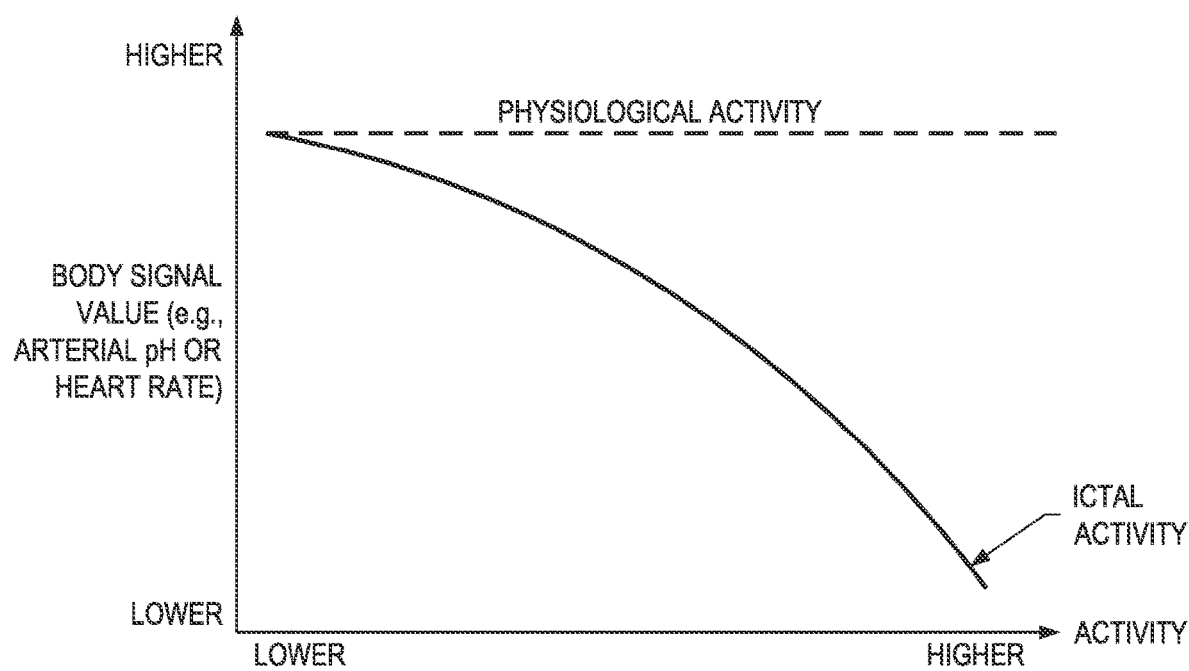
FIG. 3G shows an example of the ΔDetection, ΔNon-Ictal, and ΔIctal components of heart rates, according to some embodiments of the present disclosure.

FIGS. 3C and 3D together show that a non-pathological heart rate (or other body index such as respiratory rate, blood oxygen saturation, etc.) range may be established for a given activity level of the patient. In some embodiments, the range may be a unique range based on historical data for the patient, while in other embodiments data for patient populations may be used, at least until patient-specific data can be obtained. For simplicity, FIGS. 3C and 3D depict the upper and lower boundaries as being linear. It will be appreciated, however, that the boundaries for an actual patient would not necessarily be linear, particularly where additional factors may be considered. FIGS. 3F and 3G illustrate heart rate boundaries that vary in a nonlinear manner with increasing activity levels.

The dynamic relationship between non-pathological heart rates and activity levels may be exploited to detect pathological states such as epileptic seizures by determining when the patient's heart rate is incommensurate with the patient's activity level. By monitoring the patient's activity level and heart rate, it is possible to determine when the patient's heart rate is outside the non-pathological ranges as the patient's activity levels change over time, resulting in improved accuracy (i.e., sensitivity and specificity) in detecting pathological states such as seizures. FIG. 3E shows the patient's heart rate and the dynamically changing non-pathological heart rate range as the patient's activity levels change over time, with time shown on the x-axis and heart rate (HR) and non-pathological heart rate range shown on the y-axis. As patient activity levels change over the course of time (e.g., over the course of a day), commensurate non-pathological HR ranges may be determined and utilized to detect the onset of pathological states. A non-pathological range E1 provides a relatively low range that may correspond to sleeping or resting. A slightly higher (and narrower) range E2 may correspond to higher activity levels of the patient, and a significantly higher (but narrower still) range E3 may correspond to an exercise period, which returns to a lower (and broader) range E4 after the patient stops exercising.

FIG. 3E indicates that the width of a non-pathological body index range may change based on activity levels, optionally in view of additional factors (patient age, sex, fitness level, time of day, etc.) as discussed above. For example, at points E1 and E4, the range may relatively broad, reflecting relatively low activity levels. In contrast, at point E3, corresponding to strenuous exercise, the range may be relatively narrow, arising from the patient's heart rate approaching his or her maximum heart rate. Periods of elevated heart rate due to exertion may be highly correlated with activity level as measured by, e.g., an accelerometer.

Another example of how body signals such as heart rate may be affected by the patient's activity level is illustrated in an exemplary fashion in FIG. 3F. The upper curve 370 ($\Delta$)delineates ictal heart rate changes partially as a function of seizure intensity, duration and extent of brain/body spread and the lower curve 372 ($x$) illustrates a representative curve for non-ictal (i.e., non-seizure) heart rates corresponding to various activity levels of the patient. Both upper curve 370 and lower curve 372 may change over short or long time periods based on changes in patient-specific or environmental factors; the examples provided here are for illustrative purposes. For a particular activity level (e.g., any of activity levels F1-F5 in the FIG. 3F), the distance between the ictal heart rate threshold curve 370 and the non-ictal heart rate curve 372 indicates an expected or hypothetical value of $\Delta$Detectionmax for that activity level, since it is the difference between the patient's non-ictal heart rate for that activity level (curve 372) and the ictal heart rate threshold (curve 370). The lowest curve 374 represents heart rate value during sleep and resting wakefulness; the magnitude of the $\Delta$Detectionmax for seizures that occur during these states is greater than for those in which the patient is active. These differences in the magnitude of $\Delta$Detectionmax impact detection performance: The larger the $\Delta$Detectionmax, the greater the potential for false positive and for earlier detections and the smaller the $\Delta$Detectionmax, the greater the potential for false negative and late detections.

For patients whose heart/activity relationship resembles FIG. 3F, it may be difficult to distinguish between seizures and non-ictal heart rate changes at both high activity levels and low seizure intensities. At activity levels near the middle of the curve, the distance between the two curves may increase to a maximum value and at this point the ability to discriminate between seizure and non-seizure states may be greatest. Embodiments of the present invention may provide improved accuracy in distinguishing pathological and non-pathological states at high and low activity levels by adjusting threshold values based on activity levels.

FIG. 3G provides simplified diagram illustrating how arterial pH decreases in otherwise healthy patients during convulsions (e.g., generalized tonic-clonic seizures) and how it remains stable during physiological work or activity levels. While ictal decreases in heart rate are well documented, arterial pH (y-axis) is used in this example. Convulsions or generalized tonic-clonic seizures are associated with transient lowering of the arterial pH to an extreme value (e.g., 7.1). Other values may be established for different seizures or pathological states. For this, as well as for any other autonomic, neurologic or endocrine signals a $\Delta$NonIctal, $\Delta$Ictal or $\Delta$Detectionmax may be computed and a $\Delta$DetectionT may be chosen.

Figure 3H:
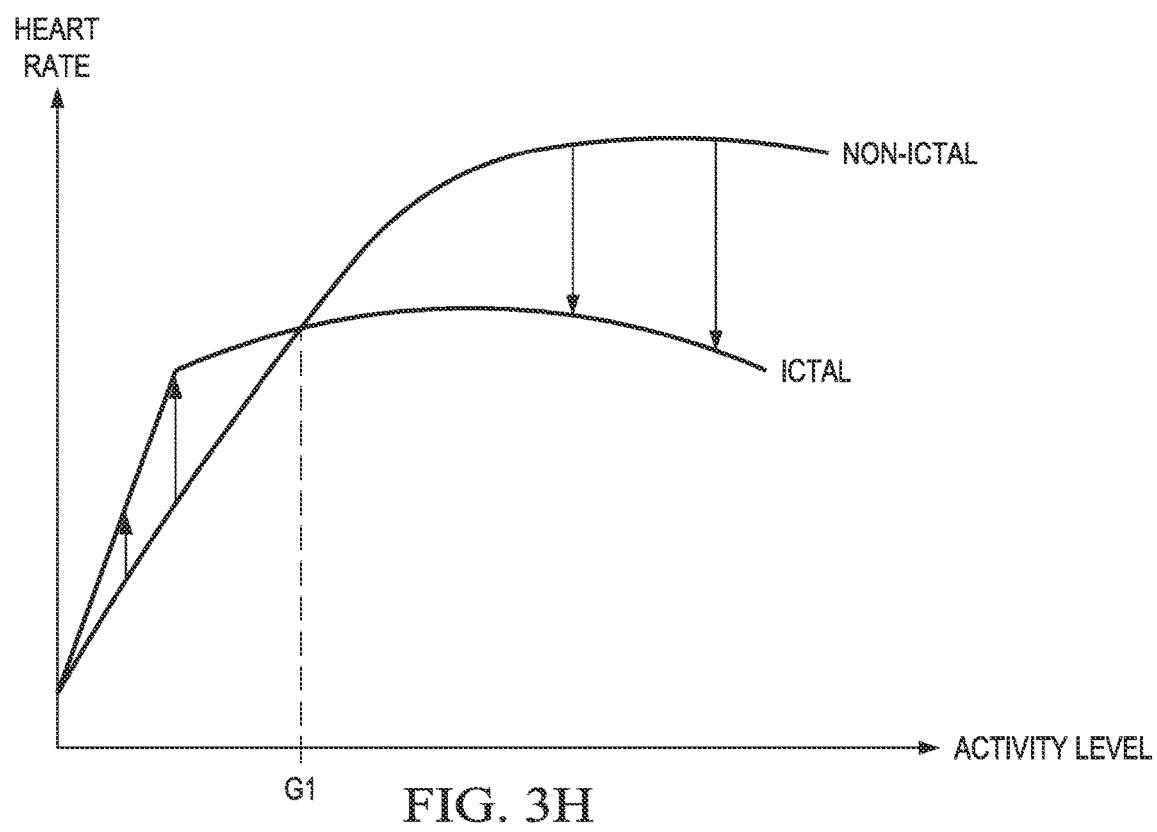
FIG. 3H shows an example of the ΔDetection, ΔNon-Ictal, and ΔIctal components of heart rates, according to some embodiments of the present disclosure.

A further example of how body signals such as heart rate may be affected by the patient's activity level and seizures is illustrated in FIG. 3H. In this figure, the heart rate represented by curve 374 and corresponding to a seizure, shows a steep initial increase (compared to that of curve 376 that shows heart rate changes as a function of activity level (x-axis)) that rapidly levels off. In this example, due to the short duration or low intensity of the seizure, the $\Delta$Ictalmax (shown by the portion of FIG. 3H in which the ictal HR exceeds the non-ictal HR for a particular activity level) was short-lived, falling below values attainable at certain physiological activity levels, making state-of-the art detection adaptation strategies such as threshold and duration constraint, potentially counterproductive. If either of the threshold (the magnitude of the change in the value of the body signal required to issue a detection) or duration constraint (time that must elapse after a signal value reached a threshold before a detection is issued) are increased beyond certain values in this case, this will result in larger numbers of false positive detection. By inherently taking into account each patient's seizures and physiological changes in signal values, seizure type or severity, and environmental conditions, embodiments of the present disclosure avoid certain state-of-the art seizure detection pitfalls. In this example, accuracy of seizure detection will be highest, as the value of ΔDetection is maximal at point H1.

At point H1, however, the slope of the ictal heart rate curve flattens, such that the non-ictal heart rate curve 376 has a higher slope (and absolute value) than the ictal heart rate threshold curve 374. Thus, at higher non-pathological increases in HR values (to the right of H1), the ictal threshold values may fall below the non-ictal heart rate thresholds. When the patient's heart rate is already elevated by exercise, the sympathetic activity may already be relatively high, and parasympathetic activity may be reduced, such that a seizure may have no further effects on sympathetic/parasympathetic balance. Consequently, the heart rate of a patient having a seizure during exercise or exertion may not increase during the seizure, and in some instances may actually decrease. By taking into account these factors and incorporating them into a detection strategy, this invention advances the state-of-the art. In short, unlike the conventional approach that attempts to optimize performance by blindly increasing the threshold and/or duration constraints, this invention may in some embodiments decrease in an informed/intelligent manner, threshold and duration constraints whenever appropriate.

For patients having seizures characterized by decreases in heart rate, the approach or strategy described for ictal HR increase may be reversed. Seizures with reduced heart rate may be associated with ictal-driven reduced sympathetic drive and/or increased parasympathetic drive. For such patients, the ictal heart rate threshold curve may lie below the non-ictal heart rate curve at lower activity levels. For detection purposes, seizures that reduce the heart rate may be easier to detect at higher activity levels than at lower activity levels. While it may not be feasible (for safety/medical reasons and due to current technological limitations) to increase activity level immediately prior to the onset seizures associated with bradycardia, use of certain physiological parameters such as maximal heart rate, resting heart rate or reserve heart rate as reference values, may overcome this inherent limitation. Additional details regarding the use of reference or fiducial heart rates to detect seizure are provided in co-pending application Ser. No. 14/170,389, filed Jan. 31, 2014, entitled "Parametric Seizure Detection, which is hereby incorporated by reference herein in its entirety. In some embodiments, the patient's heart may be paced to avoid decreases in heart rate caused by seizures associated with reduced heart rat Patient-specific seizure-detection algorithms may be developed in which seizure detection is based upon activity levels. For patients having increased heart rate associated with seizures, in whom, for example, the ability to discriminate ictal from non-ictal increases in heart rate is highest at moderate activity levels, and less reliable at low and high activity level, cardiac-based algorithms may be replaced by or complemented with algorithms that use other body signals such as movement, responsiveness/awareness, blood oxygen saturation, skin resistivity, respiration, etc. For patients having reduced heart rate during seizures, in whom, for example, the ability to discriminate ictal from nonictal decreases in heart rate is best at higher activity levels, other body signals may be used.

FIGS. 3C, 3D, and 3F provide examples of how a seizure detection index, such as heart rate, may be affected by work or activity levels of a patient, and demonstrate that activity levels may be used to dynamically adjust heart rate seizure detection thresholds to improve the accuracy of cardiac-based seizure detection algorithms. Other seizure detection indices may also be correlated to activity levels to provide improved seizure detection when cardiac-based algorithms are inapplicable or inaccurate.

Additional details as to how dynamic seizure detection thresholds may be determined for a first body data stream (such as a cardiac data stream) based on activity level or another second body data stream are provided in U.S. patent application Ser. No. 14/084,513, filed Nov. 19, 2013, to which the present application claims priority (See, e.g., FIGS. 3-5 and discussion thereof).

Figure 4:
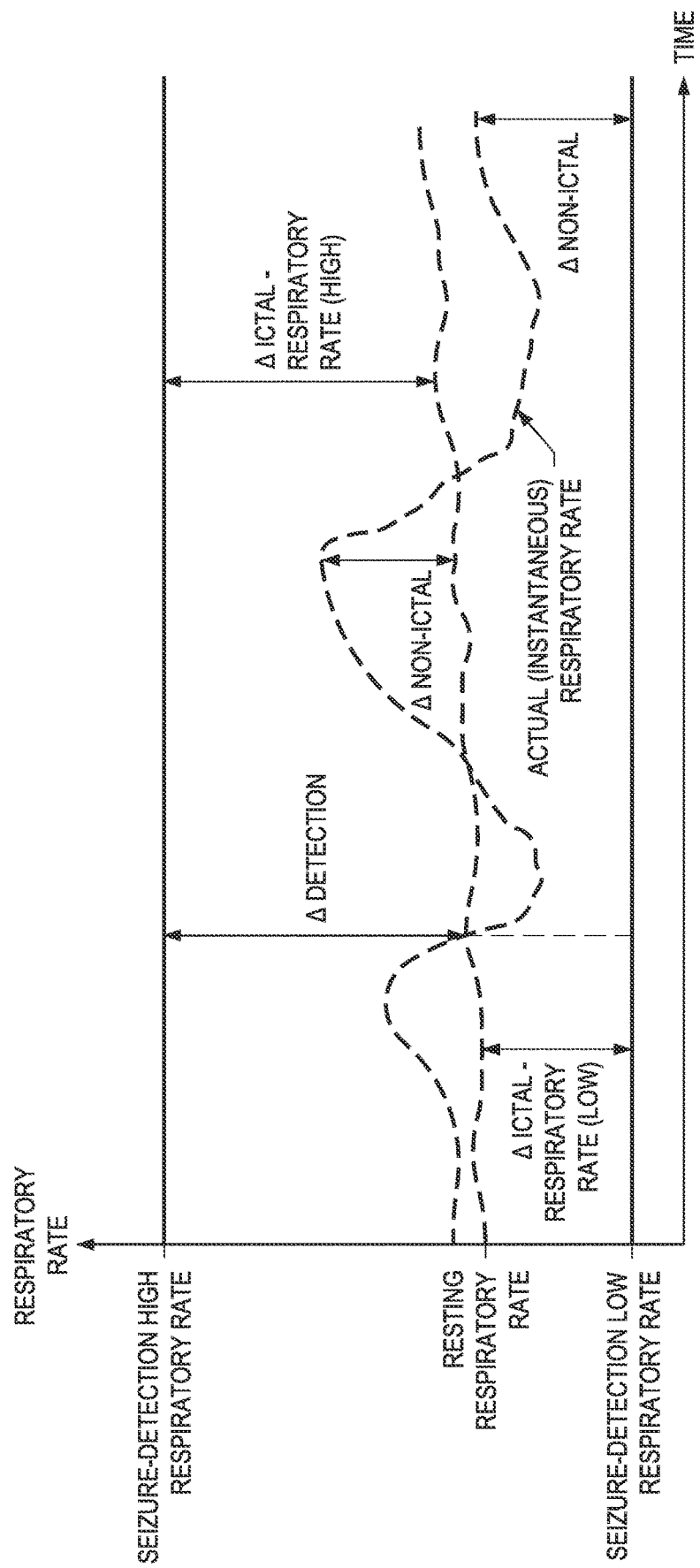
FIG. 4 shows an example of the ΔDetection, ΔNon-Ictal, and ΔIctal components of respiratory rates, according to some embodiments of the present disclosure.

FIG. 4 shows a simplified diagram of the dynamic nature of an exemplary reference respiratory rate, a current (actual or instantaneous) respiratory rate (CRR), ΔNon-Ictal, and ΔIctal components of increases in respiratory rate, and ΔDetection values, according to some embodiments of the present disclosure. The various relationships generally parallel those shown for heart rate in FIGS. 3A and 3B.

Figure 5:
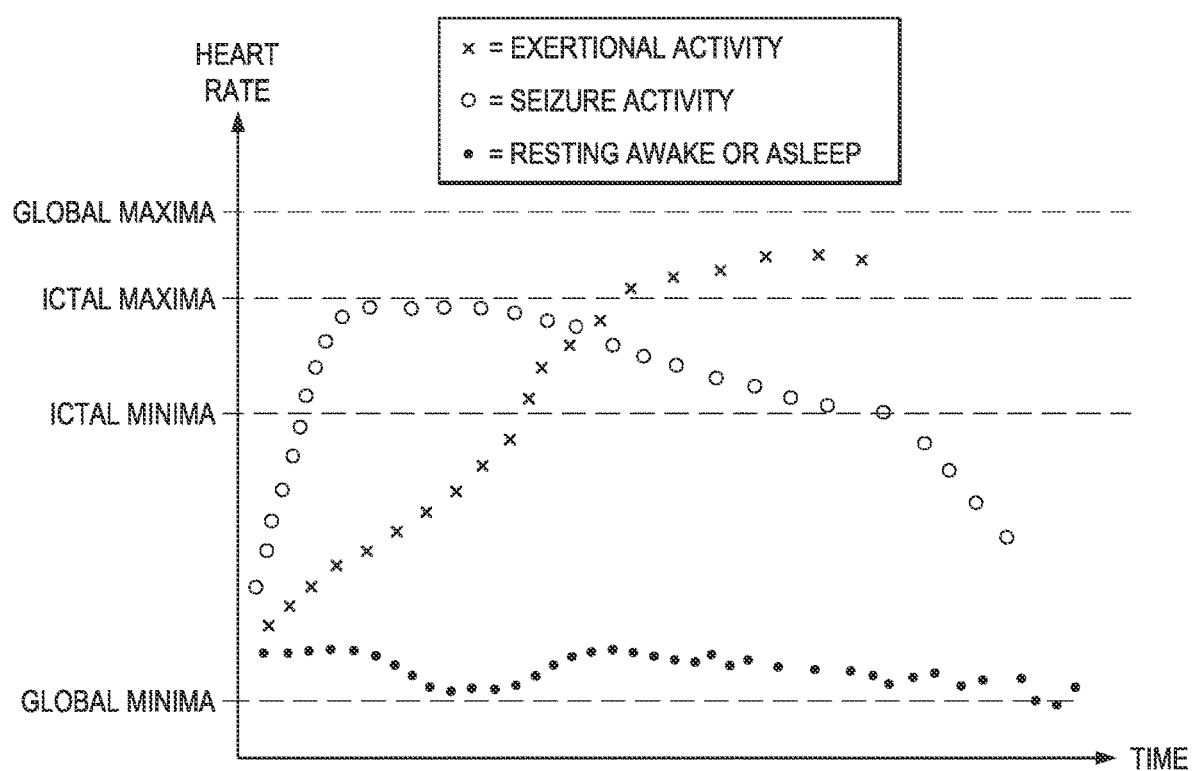
FIG. 5 shows an example of the ΔDetection, ΔNon-Ictal, and ΔIctal components of body data, according to some embodiments of the present disclosure.

FIG. 5 is an idealized representation of heart rate changes (y-axis) during sleep and resting wakefulness (●), exertional activity of various degrees of intensity (X) (x-axis) and seizures/ictal (○). Lines in dash (-) depict the lowest heart rate (global minima, such as that during certain sleep), the minimal increase in heart rate a seizure may cause (ictal minima), the maximal increase in heart rate a seizure may cause (ictal maxima) and the maximal heart rate (global maxima) given by the formula 220-age. The ictal maxima (for HR) may in convulsive seizures be equal to the global HR maxima. These curves serve as the basis for calculating increases in heart rate due to: a) exertional/physiological activity (ΔNon-Ictal); seizures (ΔIctal); and the magnitude of the detection margin (ΔDetection=ΔNon-Ictal−ΔIctal).

The minimal possible heart rate may or may not be the same as the resting heart rate and the maximal possible heart rate may or may not be the same as the maximal ictal heart rate. The resting, ictal and exertional heart rates may vary as a function of multiple factors, making the ΔDet variable in magnitude. In general, the lower the non-ictal heart (non-ictal heart rate encompasses resting and exertional heart rates) and the higher the ictal component, the larger the ΔDet. A probability index for ictal detections may be estimated based on the values of the non-ictal components of a body signal and a correction or normalization may be introduced to decrease the number of FN detections when the non-ictal component is high or the ΔIctal is low.

Although FIGS. 3A-5 are directed to heart rate or respiratory rate, other signal features, such as heart rate variability, blood pressure, respiratory rhythm, or other body signals such dermal activity, or oxygen saturation, catecholamine concentrations, brain signals (electrical, chemical, thermal, etc.) among others would also be expected to have ictal and non-ictal components of their changes, which may be identified and used to compute a delta detection.

Turning now to FIG. 6A, a stylized depiction of a heart rate change in conjunction with a kinetic index, in accordance with some embodiments herein, is shown. Those skilled in the art would appreciate that the heart rate and the kinetic index values shown in FIG. 6A are illustrated in an idealized fashion, and values of the both axes may vary and remain within the scope of the present embodiments.

FIG. 6A illustrates that initially, a patient's heart rate is relatively stable until the time 311, where the heart rate begins to rise to a second level. The medical device 200 may detect a change in the HR, wherein this detection may trigger an acquisition of another set of body data, such as a kinetic index. The medical device 200 may then perform a correlation function to determine whether the changes in the HR correlate with the changes in the kinetic index. In the example of FIG. 6A, at the time 311, at approximately the time of the change in the HR, an increase in the kinetic index is also observed. Based upon an analysis of the HR change and the increase in the kinetic index, the medical device 200 may determine that there is a correlation between the changes in these two parameters. In one embodiment, the strength of this correlation may be qualitative (e.g., low, medium, high) or quantitative (e.g., −0.8, −0.2, 0.3, 0.9). In the example of FIG. 6A, at time 311, which corresponds to the time marker labeled "1st change," the medical device 200 may determine that the change in the HR has a satisfactory correlation (e.g., is commensurate) with the corresponding change in the kinetic index. That is, the medical device 200 may determine that the change in HR is physiological in nature and has substantially no ictal component.

At the time 312, the rise in the HR levels off, as indicated in FIG. 6A. Upon detection of a change (e.g., an increase, a decrease, or a leveling off) in HR, the medical device 200 may acquire other body data to determine if the change is physiological and/or pathological. At the time 312, when the HR levels off (which corresponds to another change in the signal), the medical device 200 may acquire kinetic index data, which in this example, also levels off, indicating that the change in HR is physiological. The rise in the HR from the time period prior to the time 311, to the HR at the time 312 is the Anon-ictal value for HR at that time (i.e., the change in the HR value is of a primarily a non-ictal component, caused by non-pathological causes).

At time 313, the HR again rises, as shown in FIG. 6A. Upon the detection of the change in HR at time 313, the medical device 200 may check the behavior of the kinetic index. In the example of FIG. 6A, the kinetic index does not change at time 313. At time 313, the medical device 200 may determine that the rise in HR is not associated with a corresponding increase in the kinetic index. Accordingly, the medical device 200 may determine that change in the rise of HR at time 313 is pathological. Therefore, the rise in the HR during time period 313, from the HR during the time 312 is the $\Delta$ictalMax value for HR (i.e., the change in the HR value is of a primarily an ictal component, and as such, is pathological in a patient with epilepsy).

Turning now to FIG. 6B, a stylized depiction of a heart rate change in conjunction with a kinetic index during a seizure with prominent motor activity, in accordance with another embodiment herein, is shown. In the example of FIG. 6B, the HR and a corresponding kinetic index value remain stable during time 314. During time period 314, the HR increases, however, this increase is commensurate with the change in the kinetic index. Therefore, the rise in HR at time 314 is primarily non-pathological (Anon-ictal).

At the beginning of time period 315, the HR rises with no corresponding change in the kinetic index. In this case, the medical device 200 may determine that this change in HR is pathological ($\Delta$ictal in a patient with epilepsy). In this case, since a pathological rise in HR is detected with no contribution from kinetic activity of the patient, the medical device 200 may determine that the rise in HR (during time period 315) is primarily neurogenic ($\Delta$ictal[neurogenic]).

At the beginning of time period 316, the HR further increases, albeit with a corresponding change in the kinetic index. In this case, the further increase in HR is associated with an increase in kinetic activity, and the further increase in HR may be construed as having an exertional component (if the demand for oxygen is met) and a respiratory/metabolic component (if the demand for oxygen is not met, such as is the case in a convulsion) ($\Delta$ictalexertional/metabolic). In this example, $\Delta$ictal total is the sum of both $\Delta$ictalneurogenic and $\Delta$ictalexertional/metabolic. That is, when the patient has a seizure, the increase in HR may be primarily based upon neurogenic factors, and after a certain time period, contributions from exertion and respiratory/metabolic changes caused by the ictal state may contribute to a further rise in the HR (if the seizure spreads). In an alternative embodiment, upon detection of a change in a body signal (e.g., HR) that may be suggestive of a seizure, the medical device 200 may acquire one or more other body signals (e.g., kinetic, respiratory/metabolic, or other signals) in order to determine the various contributions to $\Delta$ictal and/or to confirm that a detection is accurate. Those skilled in the art having benefit of the present disclosure would appreciate that other body data indexes may be applied to the analysis relating to FIGS. 6A-6C.

Turning now to FIG. 6C, a stylized depiction of a heart rate change in conjunction with a kinetic index for illustrating a $\Delta$detection, in accordance with embodiments herein, is provided. FIG. 6C illustrates a resting HR 325 and a detection threshold HR 323. In some embodiments, the detection threshold HR 323 may be programmable, may be adjustable, or both. In this example, if the HR value rises above the detection threshold HR 323, an ictal state may be declared by the medical device 200. The difference between the detection threshold HR and the resting HR is $\Delta$detection [T] (delta detection threshold). Therefore, once a HR increase crosses the detection threshold 323, the medical device 200 may issue a detection of a pathological state. Upon this issuance, a responsive action may be taken, such as those described elsewhere herein. The maximum available $\Delta$detection[T] may be used to define the threshold [T] for issuing a detection when a change in HR is incommensurate with the kinetic index. If the increase in HR resulting in crossing of the detection threshold is non-ictal, e.g., the change in HR is commensurate with the kinetic index, a detection may not be issued. However, in certain situations, if the HR exceeds a maximum detection threshold, a detection may be issued regardless of any non-ictal component of HR.

In the example of FIG. 6C, the HR and a corresponding kinetic index value remain stable up to time 317. At time 317, the HR increases, wherein this increase is commensurate with a corresponding change in the kinetic index, as shown in FIG. 6C. The rise in HR due to the kinetic activity corresponding to time 317 peaks at time 318 and is deemed to be non-pathological (Anon-ictal).

At time 319, the HR increases substantially, and ultimately rises above the detection threshold HR. Moreover, the rise in HR at time 319 fails to coincide with a rise in the kinetic index. As such, the medical device 200 may determine that this rise in HR (at time 319) is due to a pathological condition. The rise in HR continues to a maximum HR value at time 321, after which the HR decreases. The rise in HR from the baseline value to the peak value at time marker 321 is $\Delta$ictal[max]. In some embodiments, where the detection threshold is set relative to $\Delta$ictal[max] may vary based on the clinical application, wherein in some clinical applications the detection threshold may be set at a higher level than in other clinical applications. For example, if rapid detection or high sensitivity is more desirable, the detection threshold may be set at a lower level, than in cases where accuracy of detection is more desirable.

In the example of FIG. 6C, the patient's HR remains relatively stable until time 322, where a rise in kinetic index appears immediately prior to this time. At time 322, the HR rise is commensurate with the rise in the kinetic index (Anon-ictal). In this example, the HR continues to rise incommensurately ($\Delta$ictal) with the kinetic index, which indicates a pathological state. The difference between this maximum HR value and the Anon-ictal value is $\Delta$ictal[max]. In other words, when during this time period, the HR crosses the detection threshold and comprises an ictal component, the system may declare a seizure.

Moreover, after a decline in the kinetic index in time period 322, the HR decreases below the resting HR. In some examples, at least a portion of this decline may be due to a non-pathological cause, and another portion may be the result of a pathological event. In some embodiments, the medical device 200 may determine a $-\Delta$non-ictal and a $-\Delta$ictal. The analysis described above with respect to crossing the detection threshold above the resting HR may be applied to crossing a second detection threshold below the resting HR (not shown). Other body data indexes (e.g., respiratory index, endocrine index, neurologic index, etc.) may also be used in analyses similar to those exemplified in FIGS. 6A-6C.

Figure 6D:
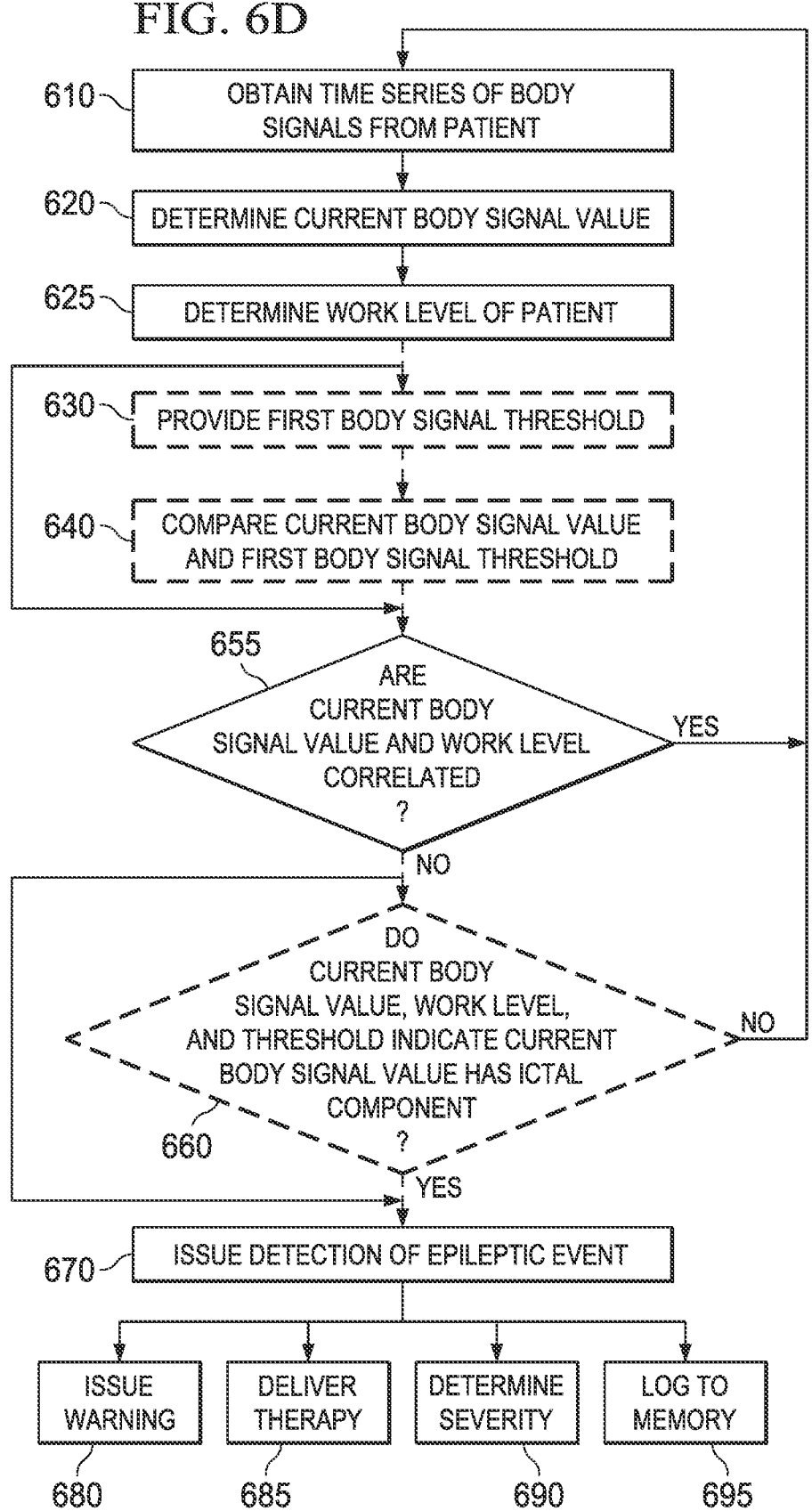
FIG. 6D shows a flowchart depiction of a method, according to some embodiments of the present disclosure.

FIG. 6D shows a flowchart representation of a method 600, according to some embodiments of the present disclosure. A time series of body data from a patient may be obtained (block 610). The time series of body data may comprise one or more body data streams suitable for detection of seizures, such as a cardiac signal, a respiratory signal, a blood oxygen saturation signal, etc. A current body signal value may be determined (block 620) from said time series. The current body data value may comprise one or more of a current heart rate, a current respiratory rate, a current blood oxygen saturation, etc. A work level of the patient may be determined (block 625). The work level determination may take into account at least in part one or more of a time of day, an indicator of said patient's overall health, an indicator of said patient's overall fitness, an indicator of said patient's level of consciousness (e.g., wakefulness v. sleep), the ambient temperature, the ambient humidity, or other patient or environmental conditions.

In some embodiments, upon the determination of work level (block 625), the method may proceed to a determination (block 655) whether the current body signal value and the work level are commensurate. (This determination will be described in more detail below). Optionally, upon the determination of work level (block 625), the method may comprise providing at least a first body signal threshold (generally, a pathological threshold, e.g., an ictal threshold) (block 630). In one embodiment, the first body signal threshold may be set based on the current body signal value. The current body signal value may be compared (block 640) with the first body signal threshold. For example, the comparison (block 640) may comprise a determination that the current body data value exceeds an ictal threshold.

Regardless of whether the optional embodiments at blocks 630 and 640 are performed, the method 600 may comprise a determination whether the current body signal value and the work level are commensurate (block 655). If they are commensurate, then it can reasonably be concluded that the patient is not currently undergoing a pathological state, e.g., an epileptic event, e.g., a seizure. Upon a finding of commensurateness (block 655), the method 600 may return to obtaining the time series of body signals (block 610).

On the other hand, a finding of a lack of commensurateness (block 655) may, but does not necessarily, indicate the patient is currently suffering a pathological state, e.g., an epileptic event, e.g., a seizure. Thus, optionally, a determination may be made (block 660) as to whether the current body signal value comprises an ictal component. In one embodiment, the current body signal value may be considered to have an ictal component if its value is in a range that, based on the current work level and a threshold provided at block 630, indicates an ictal component. At minimum, the current body signal only has an ictal component if its value is incommensurate with work level. In one embodiment, the current body signal value has an ictal component if it exceeds an ictal threshold for the body signal value for a given activity or work level. In an alternative embodiment, the current body signal value has an ictal component if it exceeds one of the exertional component or a $\Delta$Non-Ictal value of the body signal value. For resting states (sleep or awake) the non-exertional component to certain body signals such as heart or respiratory rate is negligible. For other body signals such as neuronal electrical signals, the exertional component is negligible. The determination (block 660) as to whether the current body signal value comprises an ictal component may be based on the work level (determined block 625) and the comparing (block 640). In one embodiment, ictal and non-ictal components and $\Delta$Detection values may be calculated and used to estimate the accuracy of a detection. Based on the probability of detection accuracy, corrections or normalizations may be performed that may result in the issuance or non-issuance of a seizure detection.

If the determination (block 660) is that the current body signal value comprises the ictal component, then a detection of an epileptic event, (e.g., a seizure) may be issued (block 670), subject in at least one embodiment to the ictal component having a certain magnitude for a certain time period. Thereafter, at least one further action may be taken, such as issuing (block 680) a warning of the epileptic seizure to the patient, a caregiver, or a physician; delivering (block 685) a therapy, such as a vagus nerve electrical stimulation therapy using an implantable neurostimulator commercially available from Cyberonics, Inc., among other therapy modalities known to the skilled artisan; quantifying (block 690) a severity of the epileptic seizure; and logging to memory (block 695) one or more of the date and time of occurrence of the epileptic seizure, the severity of the epileptic seizure, a type of therapy delivered, or at least one effect of the therapy. Thereafter, flow may return (not shown) to obtaining (block 610).

If the determination (block 660) is that the current body signal value lacks the ictal component, then flow may return to obtaining (block 610).

Therefore, in one embodiment, method 600 may comprise seizure detection based on a correlation (or lack thereof) between the current body signal value (which may be considered a dependent variable) and work level (which may be considered an independent variable).

FIG. 7A shows a flowchart representation of providing a body signal threshold (block 630) according to some embodiments. At least one time series of body data may be received (block 710). Signals usable in embodiments of the present invention may include a cardiac signal, a respiratory signal, etc., which may be tested for the presence of an ictal component in (and thus for decorrelation or incommensurateness with) a work or activity level. In some embodiments, previously received and/or processed reference body data, such as that previously collected from the patient over a period of days, months or years, may also be looked up in a table (block 720). In some embodiments, the table look up (block 720) may comprise correlating the time series of body data with looked-up reference body data from block 720. For example, it may be found that a current time series of body data received (block 710) is poorly correlated with the looked-up reference body data (block 720), thus suggesting that the patient's condition may have changed or the detection apparatus may be malfunctioning. (The reference data may be at least in part a function of the activity level and/or other factors). In some embodiments, the table look up (block 720) may be based at least in part on the patient's work level (determined at FIG. 6, block 625).

A reference body signal value may be determined (block 740). In some embodiments, the reference body signal value may comprise an ictal threshold function, or an ictal value for a body data signal value. The first body signal reference value may be determined from one or more of the at least one time series of body data received (block 710), or the looked-up reference body day from block 720.

Turning now to FIG. 7B, a stylized depiction of a table for providing a reference value for the dependent variable (e.g., HR), that should correspond to a certain work or activity level (the independent variable) as indicated in FIG. 7A, in accordance with some embodiments, is illustrated. In one embodiment, upon determining the work level of the patient, the medical device 200 may perform a look up of body data values in a table (e.g., such as the table of FIG. 7B) in order to provide a physiological reference value (e.g., mean, median, range (max.-min)) for the algorithm described in FIG. 6D. The table exemplified in FIG. 7B comprises work level values that each correspond with activity types. For each work level and activity type, the table may provide reference body data values obtained from a given patient or from a group of patients under physiological conditions. The endosomatic (e.g., level of consciousness, etc.) and exosomatic (e.g., ambient temperature) conditions under which the body data values were obtained may be documented in the look-up table to allow valid comparisons. These body data values may be used by the algorithm exemplified in FIG. 6D to perform comparisons. Those skilled in the art having benefit of the present disclosure would appreciate that additional work levels, activity types, and body data values may be provided in the table of FIG. 7B.

In the example of FIG. 7B, the work level (work level 1, 2, 3, etc.) may be used to select an activity type (activity type A, B, C, etc.) that corresponds to the work level. In one embodiment, the medical device 200 may make a determination of the type of activity that the patient is engaged in based upon the detected work level. For example, for a particular patient, as shown in FIG. 7B, "work level-3" may correspond to "activity type-C" (walking). In an alternative embodiment, based upon sensed body signal(s), the medical device 200 may determine the type of activity (e.g., REM sleep, walking, running, etc.) in which the patient is engaging. In one embodiment, this may be used as a verification function in order to determine that the work level corresponds to the activity type. In some embodiments, determination of the activity level may allow determination of the work level.

The medical device 200 may look up the value of a particular body data (1st body data value, 2nd body data value, etc.) for the determined work level and the corresponding activity level. For example, if the medical device 200 determines that the value of the work level is substantially equal to "work level-3," the medical device 200 may make an assumption that the patient is walking ("activity type-C"). In some embodiments, the medical device 200 may verify the activity type. This verification may be based upon detected body signal(s) and/or input received from an external source, e.g., an observer or caregiver. The corresponding reference body data value ("1st body data value") in this example is a heart rate of 82 beats per minute (BPM). This heart rate value may be used as a reference value to determine whether the current body signal is commensurate with the patient's activity or work level.

As another example, if the detected work level has a value of "work level-2," the medical device 200 may make an assumption that the patient is in a non-REM sleep state ("activity type-B"). In some embodiments, the medical device 200 may verify the activity type. The reference 3rd body data value corresponding to this example is a respiratory rate (RR) of 8 breaths per minute (BrPM). This respiratory rate value may be used as a reference or threshold value to determine whether the work level is commensurate with patient activity. Similarly, a plurality of body data values may be used as a threshold value to determine whether the detected work level is commensurate with patient activity. In some embodiments, the table may contain data about mental (e.g., cognitive, emotional) activity so that determination of an ictal content (if any) in the current body signal (e.g., the dependent variable) value may be accurately made.

Those skilled in the art having benefit of the present disclosure would appreciate that other types of look-up tables may be used to determine reference or threshold body data values and remain within the spirit and scope of the embodiments disclosed herein.

The methods depicted in FIGS. 6D-7A and described above may be governed by instructions that are stored in a non-transitory computer readable storage medium and that are executed by, e.g., a processor 217 of the medical device 200. Each of the operations shown in FIGS. 6D-7A may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

In other embodiments (not shown), the present disclosure relates to a method for detecting an epileptic seizure based upon a comparison between at least two time series of body signals from a patient, comprising: obtaining a first body signal time series from said patient; determining a current body signal value from said first body time series; obtaining a second body signal time series from said patient; determining a current body signal value from said second body time series; comparing said current first body signal value and said at least a second body signal value; determining based on said comparing whether or not the change between first and said first body signal is commensurate or is correlated; determining whether said current body signal value comprises an ictal component, based on a determination that said change in said first body signal value is incommensurate or uncorrelated with said value in said second body signal; issuing a detection of an epileptic seizure in response to said determination that said current body signal value comprises an ictal component; and taking at least one responsive action to said issuing, wherein said responsive action is selected from issuing a warning of said detection, delivering a therapy, determining a severity of the detected epileptic seizure, and logging to memory one or more of the date and time of occurrence of the detection of the epileptic seizure, a severity of the detected epileptic seizure, a type of therapy delivered to treat the epileptic seizure, or at least one effect of a therapy delivered to treat the epileptic seizure. In one embodiment, the strength and direction of the correlation between said at least first body signal time series and said at least second body signal time series may be determined. By way of example, the strength of the correlation may be determined to be low, medium or high or quantified and expressed as value [0-1] and the direction may be positive or negative. For a first body signal (e.g., heart rate) whose values move in the same direction as those of the second body signal (e.g., kinetic activity), that is when one increase the other also increase, and a decrease in one is accompanied by a decrease in the other, the correlation is positive and for those for which one value decreases while the other increases (e.g., vagus nerve activity and heart rate) the correlation is negative. The absolute magnitude of the value of a correlation may be used to determine if there is an ictal component (see [004]) or a change in their pattern may be sufficient to make this determination. In one embodiment, the at least first and at least second body signals are different.

In some embodiments, this disclosure provides a method for identifying and using natural or innate body signal thresholds for identifying transitions between a non-pathological and pathological and the transition back to normalcy by determining using at least two body signals, the contribution to changes in said signal value of physiologic or non-pathologic factors versus those of non-physiologic or pathologic factors. In a patient with epilepsy in which heart rate increases due to non-pathologic factors such as jogging and also to seizures, parsing out the contributions from each physiologic and each pathologic factor contributing to changes in body signals values, allows for accurate determination of the transition from one state to the other. Coming back to epileptic seizures, classification of changes in a body signal (e.g., HR) into non-ictal (i.e., caused by exercise) and into ictal (caused by a seizure) and their quantification (for example, in beats/min for HR) leads to the identification of non-ictal body signal thresholds that among other factors, depend on level and type of physical activity. Let us say that the HR of a patient with epilepsy walking at speed $v_1$ on a level surface increases by an average of 20 bpm compared to when the patient is standing still. The +20 bpm may be used in this case as the seizure detection threshold each time the patient walks at speed $v_1$ on a level surface, all other things equal. In this patient a seizure detection may then be issued if and when the HR exceeds the ΔNon-ictal (+20 bpm) by an integer (e.g., 25 bpm–20 bpm=5) or non-integer value n, an increase over the reference value (+20 bpm) in this case that is referred herein to as ΔIctal.

In some embodiments, the present disclosure relates to one or more of the following numbered paragraphs:

51. A non-transitory computer readable program storage unit encoded with instructions that, when executed by a computer, perform a method for detecting an epileptic seizure based upon a time series of a patient's body data, comprising:
determining a reference body data value;
determining a short-term body data value;
determining at least one body data delta value, based on at least a difference between said reference body data value and said short-term body data value; and
detecting said epileptic seizure, based on said at least one body data delta value.

52. The non-transitory computer readable program storage unit of numbered paragraph 51, wherein determining said reference body data value comprises:
receiving a reference time series of said body data;
looking up a prior reference body data in a table;
comparing said reference time series and said prior reference body data; and
setting said reference body data value, based on said comparing.

53. The non-transitory computer readable program storage unit of numbered paragraph 51, wherein said short-term body data value is determined based upon a foreground time series of body data.

54. The non-transitory computer readable program storage unit of numbered paragraph 51, said method further comprising:
determining an occurrence of an epileptic seizure, in response to said short-term body data value exceeding a seizure detection threshold;
performing at least one further action selected from treating the seizure, issuing a warning regarding the seizure, or logging the seizure or the severity thereof, in response to said epileptic seizure being determined to have occurred; and
providing said short-term body data value to a unit to said determining said at least one body data delta value, in response to said epileptic seizure being determined not to have occurred.

101. A non-transitory computer readable program storage unit encoded with instructions that, when executed by a computer, perform a method for detecting an epileptic seizure based upon a time series of beats of a patient's heart, comprising:
obtaining said time series of heart beats;
determining a reference heart rate value from said heart beats in a first time window;
determining a second heart rate value from said heart beats in a second time window, wherein said second time window is shorter than said first time window;
determining a third heart rate value from said heart beats in a third time window, wherein said third time window is shorter than said second time window;
determining a non-ictal component of said patient's heart rate value, wherein said non-ictal component equals said second heart rate value minus said reference heart rate value;
determining an ictal component of said patient's heart rate value, wherein said ictal component equals said third heart rate value minus said reference heart rate value;
determining a seizure detection delta, wherein said seizure detection delta equals said ictal component minus said non-ictal component; and
detecting said epileptic seizure, based at least in part on said seizure detection delta exceeding a seizure detection threshold.

102. The non-transitory computer readable program storage unit of numbered paragraph 101, wherein said first time window comprises from about 60 sec to about 24 hr.

103. The non-transitory computer readable program storage unit of numbered paragraph 101, wherein said second time window comprises from about 1 sec to about 60 sec.

104. The non-transitory computer readable program storage unit of numbered paragraph 101, wherein determining said non-ictal component comprises measuring a body signal relating to a work level of said patient, wherein said measuring is performed by one or more of an accelerometer, an inclinometer, an electromyography (EMG) sensor, a muscle temperature sensor, an oxygen consumption sensor, a lactic acid accumulation sensor, a sweat sensor, a neurogram sensor, a force transducer, or an ergometer.

105. The non-transitory computer readable program storage unit of numbered paragraph 101, wherein determining said non-ictal component is based at least in part on one or more of a time of day, an indicator of said patient's overall health, an indicator of said patient's overall fitness, or an indicator of said patient's wakefulness.

106. The non-transitory computer readable program storage unit of numbered paragraph 101, further comprising dynamically adjusting said seizure detection threshold based at least in part on one or more of a time of day, an indicator of said patient's overall health, an indicator of said patient's overall fitness, an indicator of said patient's wakefulness, a time since a most recent previous seizure, an average inter-seizure interval, a severity of a most recent previous seizure, or an average seizure severity.

201. A medical device system, comprising:
at least one first sensor configured to collect data relating to a time series of beats of a patient's heart;
at least one second sensor configured to collect data relating to said patient's work level; and
a medical device, comprising:
a current body signal module configured to obtain a time series of heart beats from said collected body data; to determine a reference body data value from said heart beats in a first time window; and to determine a short-term body data value from said heart beats in a second time window, wherein said second time window is shorter than said first time window;
a ictal component module configured to determine a non-ictal component of said short-term body data value, based at least in part on said data relating to said work level; to determine an ictal component of said short-term body data value, wherein said ictal component equals said short-term body data value minus said reference body data value; and to determine a seizure detection delta, wherein said seizure detection delta equals said ictal component minus said non-ictal component; and
a seizure detection module configured to detect an epileptic seizure, based at least in part on said seizure detection delta exceeding a seizure detection threshold.

202. The medical device system of numbered paragraph 201, wherein said at least one second sensor is selected from an accelerometer, an inclinometer, an electromyography (EMG) sensor, a muscle temperature sensor, an oxygen consumption sensor, a lactic acid accumulation sensor, a sweat sensor, a neurogram sensor, a force transducer, or an ergometer.

203. The medical device system of numbered paragraph 201, further comprising an additional factor module configured to determine at least one additional factor selected from a time of day, an indicator of said patient's overall health, an indicator of said patient's overall fitness, or an indicator of said patient's wakefulness; and
wherein said ictal component module is configured to determine a non-ictal component of said short-term body data value, based at least in part on said at least one additional factor.

204. The medical device system of numbered paragraph 201, wherein said epileptic seizure detection module is configured to dynamically adjusted said seizure detection threshold based at least in part on one or more of a time of day, an indicator of said patient's overall health, an indicator of said patient's overall fitness, an indicator of said patient's wakefulness, a time since a most recent previous seizure, an average inter-seizure interval, a severity of a most recent previous seizure, or an average seizure severity.

205. A method for detecting an epileptic seizure based upon a time series of beats of a patient's heart, comprising:
obtaining said time series of heart beats;
determining a current heat rate from said time series of heart beats;
providing a first reference heart rate value, providing a second reference heart rate value, determining at least one of
a non-ictal component of said patient's heart rate value, wherein said non-ictal component equals said current heart rate value minus said second reference heart rate value;
a delta detection component of said patient's heart rate value, wherein said delta detection component equals said first reference heart rate value minus said current heart rate value; and
a delta ictal value, wherein said delta ictal value equals said first reference heart rate value minus said second reference heart rate value; and
determining at least one of
a risk of a false positive detection,
a risk of a false negative detection, and
the occurrence of an epileptic seizure,
wherein said determining is based on at least one of said delta non-ictal value, said delta detection value, and said delta ictal value.

206. The method of claim 205, wherein said first reference heart rate value is an ictal threshold of heart rate as a function of patient activity level.

207. The method of claim 205, wherein said second reference heart rate value is a resting heart rate of the patient.

301. A method for detecting an epileptic seizure based upon a time series of body signals from a patient, comprising:
determining a current body signal value from a time series of body data from said patient;
determining a work level of said patient; and
determining whether said current body signal value comprises an ictal component, based on said work level;
issuing a detection of an epileptic seizure in response to said determination that said current body signal value comprises an ictal component; and
taking at least one action selected from issuing a warning of said detection,
delivering a therapy,
determining a severity of the detected epileptic seizure, and logging to memory one or more of
the date and time of occurrence of the epileptic seizure,
a severity of the epileptic seizure,
a type of therapy delivered to treat the epileptic seizure, or
at least one effect of a therapy delivered to treat the epileptic seizure.

302. A method for detecting an epileptic seizure based upon a time series of body signals from a patient, comprising:
receiving a time series of a first body signal from the patient;
receiving a time series of a second body signal from the patient;
determining if there is a change in said time series of said first body signal;
determining if there is a change in said time series of a second body signal that correlates to a change in said time series of a first body signal, in response to determining that there is a change in said time series of a first body signal, detecting an epileptic seizure in response to determining that there is no change in said time series of a second body signal that correlates to a change in said time series of a first body signal;
performing a responsive action in response to detecting an epileptic seizure, wherein said responsive action comprises at least one of delivering a therapy, providing a warning, and logging data relating to said epileptic seizure.

303. The method of claim 302, wherein performing a responsive action is selected from
delivering a therapy comprising at least one of an electrical therapy to a target nerve structure and a drug therapy;
providing a warning comprises a warning to the patient or a caregiver, wherein the warning is at least one of an auditory warning, a visual warning, a tactile warning, an email, a text message, and telephone call; and
logging at least one of
the date and time of occurrence of the epileptic seizure,
a severity of the epileptic seizure,
a type of therapy delivered to treat the epileptic seizure, or
at least one effect of a therapy delivered to treat the epileptic seizure.

304. The method of claim 303, further comprising determining an ictal component of said change in said first body signal in response to detecting an epileptic seizure, wherein said ictal component is based upon a different between a value of said first body signal prior to detecting an epileptic event and a value of said first body signal after detecting said epileptic event.

305. The method of claim 304, wherein said ictal component comprises the difference between the value of said first body signal prior to determining that there is no change in said time series of a second body signal that correlates to a change in said time series of a first body signal, and a value of said first body signal after determining that there is no change in said time series of a second body signal that correlates to a change in said time series of a first body signal.

306. The method of claim 302, further comprising
determining a first body index time series from said time series of said first body signal,
determining a second body index time series from said time series of said second body signal;
wherein determining if there is a change in said time series of said first body signal comprises determining if there is a change in said first body index time series; and
wherein determining if there is a change in said time series of a second body signal that correlates to a change in said time series of a first body signal comprises determining whether there is a change in said second body index time series that correlates to a change in said first body index time series.

401. A method for detecting an epileptic seizure based upon a comparison between at least two time series of body signals from a patient, comprising:
obtaining a first body signal time series from said patient;
determining a current body signal value from said first body time series;
obtaining a second body signal time series from said patient; determining a current body signal value from said second body time series;
comparing said current first body signal value and said at least a second body signal value;
determining based on said comparing whether or not the change between first and said first body signal is commensurate or is correlated;
determining whether said current body signal value comprises an ictal component, based on a determination that said change in said first body signal value is incommensurate or uncorrelated with said value in said second body signal;
issuing a detection of an epileptic seizure in response to said determination that said current body signal value comprises an ictal component;
and taking at least one responsive action to said issuing, wherein said responsive action is selected from issuing a warning of said detection, delivering a therapy, determining a severity of the detected epileptic seizure, and logging to memory one or more of the date and time of occurrence of the detection of the epileptic seizure, a severity of the detected epileptic seizure, a type of therapy delivered to treat the epileptic seizure, or at least one effect of a therapy delivered to treat the epileptic seizure.

402. The method of numbered paragraph 401, further comprising determining the strength and direction of the correlation between said at least first body signal time series and said at least second body signal.

403. The method of numbered paragraph 402, further comprising determining a presence of an ictal component based at least in part on the absolute magnitude of the change in the value of the correlation.

404. The method of numbered paragraph 402, further comprising determining a presence of an ictal component based at least in part on a change in a pattern of the correlation 405. The method of numbered paragraph 401, wherein the at least first and at least second body signals are different.

501. A method for identifying and using natural or innate body signal thresholds for identifying a transition from a non-pathological to a pathological state or a transition from a pathological to a non-pathological state, comprising:
determining at least two body signals, and
determining a first contribution to changes in the value of each said body signal from physiologic or non-pathologic factors and a second contribution from non-physiologic or pathologic factors.

In some embodiments, the present disclosure relates to a method for detecting an epileptic seizure based upon a time series of a patient's body data, comprising: determining a reference body data value; determining a present body data value; determining at least one body data delta value, based on at least a difference between said reference body data value and said body data value; and detecting said epileptic seizure, based on said at least one body data delta value.

In other embodiments, the present disclosure relates to a method for detecting an epileptic seizure based upon a time series of beats of a patient's heart, comprising: obtaining said time series of heart beats; determining a first, reference heart rate value from said heart beats in a first, long-term time window; determining a second heart rate value from a measure of central tendency of heart beats in a second, second, time window, wherein said second time window is shorter than said first time window; determining a third heart rate value from a measure of central tendency of said heart beats in a third, short-term, time window, wherein said third time window is shorter than said second time window; determining a non-ictal component of said patient's heart rate value, wherein said non-ictal component equals said second heart rate value minus said reference heart rate value; determining an ictal component of said patient's heart rate value, wherein said ictal component equals said third heart rate value minus said reference heart rate value; determining a seizure detection delta, wherein said seizure detection delta equals said ictal component minus said non-ictal component; and detecting said epileptic seizure, based at least in part on said seizure detection delta exceeding a certain value and/or a seizure detection threshold.

What is claimed:

1. A method for detecting an epileptic seizure via one or more medical devices comprising:
    obtaining one or more body signals from a patient;
    determining the patient's physiologic work level;
    determining a direction, a latency, a magnitude, a rate, and a duration of a first change in the one or more body signals;
    based on the direction, the latency, the magnitude, the rate, and the duration of the first change in the one or more body signals occurring, determining if there is a correlated change in the patient's physiologic work level;
    based on the correlated change in the patient's physiologic work level being present,
    initiating one or more actions from: delivering an electrical therapy to the patient and delivering a drug therapy.

2. A method for detecting an epileptic event in a patient's body via one or more medical devices, comprising:
    receiving a first body signal during a first time period;
    receiving a second body signal during the first time period;
    determining a work level;
    determining whether there is a change in a direction, a latency, a magnitude, a rate, and a duration of the first body signal during the first time period;
    determining a change in the work level; and
    performing a responsive action in response to detecting the epileptic event, the responsive action being delivering an electrical therapy.

3. The method of claim 2, wherein detecting the epileptic event further comprises:
    determining a non-ictal component of the change in the first body signal based upon a contribution by a physiological or non-pathological activity in the patient's body that relates to the change in the second body signal; and
    determining an ictal component of the change in at least one of: the first body signal and the second body signal based upon a difference between an entirety of the change in the first body signal, and a non-ictal component.

4. The method of claim 2, further comprising determining an ictal component of the change in at least one of: the first body signal and the second body signal, in response to detecting the epileptic event, wherein the ictal component is based upon a difference between a value of the first body signal prior to the detecting the epileptic event and a value of the first body signal during the detecting the epileptic event.

5. The method of claim 2, further comprising determining whether the work level and the second body signal are physiologic equivalencies by:
    determining an index between the first body signal and the second body signal, and
    comparing the index with at least a first value; and
    wherein calculating that there is a change in the second body signal that is physiologic equivalent with the change in the first body signal based on the index is at or above the first value;
    wherein the determination of physiologic equivalent is based on the first value being reached.

6. The method of claim 2, further comprising determining whether there is the change in the second body signal during the first time period that is physiologic equivalent with the change in the first body signal based on an occurrence of a commensurate state between the first body signal and the second body signal;
    wherein the commensurate state determination is based on a value being reached.

7. The method of claim 6, further comprising determining the commensurate state between the first body signal and the second body signal is based on an emergence of an ictal component in the first body signal and the second body signal.

8. The method of claim 2, further comprising determining a first body index from the first body signal and determining a second body index from the second body signal.

9. The method of claim 2, further comprising quantifying a physiologic equivalent level of the change in the first body signal and a change in the second body signal.

10. The method of claim 2, wherein the first body signal and the second body signal are different autonomic body signals.

11. The method of claim 2, wherein the first body signal is an autonomic signal and the second body signal is a neurologic signal.

12. A method for detecting an epileptic seizure via one or more medical devices comprising:
    obtaining one or more of an autonomic, an endocrine, a metabolic, a tissue stress, or a neurologic body signals from a patient;
    determining a direction, a latency, a magnitude, a rate, and a duration of a first change in one or more characteristics of the autonomic, the endocrine, the metabolic, the tissue stress, or the neurologic body signals has occurred;
    based on the first change in the one or more characteristics of the autonomic, the endocrine, the metabolic, the tissue stress, or the neurologic body signals having occurred, determining a change in a physiologic work performed by the patient;

in response to the determination that the change in the physiologic work has occurred, further determining the physiologic work and the one or more characteristics of the autonomic, the endocrine, the metabolic, the tissue stress, or the neurologic body signals from the patient are related;

issuing an epileptic seizure detection in response to the determination that the physiologic work and the one or more characteristics of the autonomic, the endocrine, the metabolic, the tissue stress, or the neurologic body signals from the patient are related;

delivering at least one of a drug therapy and an electrical therapy; and initiating at least one of: issuing a warning; and logging a time, a date or a severity of the epileptic seizure to a memory.

13. The method of claim 12, wherein the physiologic work is a change in energy consumption correlated with the first change in at least the one or more of the autonomic, the endocrine, the metabolic, the tissue stress, or the neurologic body signals.

* * * * *